(12) United States Patent
Cundiff et al.

(10) Patent No.: US 11,963,686 B1
(45) Date of Patent: Apr. 23, 2024

(54) SURGICAL SYSTEMS AND METHODS INCLUDING CUTTING AND ALIGNING GUIDES FOR PERFORMING AN OSTEOTOMY

(71) Applicant: Fusion Orthopedics USA, LLC, Mesa, AZ (US)

(72) Inventors: Adam J. Cundiff, Gilbert, AZ (US); Nathan G. Peterson, Gilbert, AZ (US); Mark William Roberts, Jr., Gilbert, AZ (US); Eli W. Jacobson, Chandler, AZ (US); William J. Bush, Rockford, IL (US)

(73) Assignee: Fusion Orthopedics USA, LLC, Mesa, AZ (US)

( * ) Notice: Subject to any disclaimer, the term of this patent is extended or adjusted under 35 U.S.C. 154(b) by 0 days.

(21) Appl. No.: 18/304,236

(22) Filed: Apr. 20, 2023

(51) Int. Cl.
*A61B 17/15* (2006.01)
*A61B 17/17* (2006.01)

(52) U.S. Cl.
CPC ........ *A61B 17/151* (2013.01); *A61B 17/1775* (2016.11); *A61B 17/152* (2013.01); *A61B 17/1703* (2013.01); *A61B 17/1732* (2013.01); *A61B 17/1735* (2013.01); *A61B 17/1739* (2013.01)

(58) Field of Classification Search
CPC ... A61B 17/151; A61B 17/152; A61B 17/154; A61B 17/155; A61B 17/157; A61B 17/17; A61B 17/1703; A61B 17/1732; A61B 17/1735; A61B 17/1739; A61B 17/1775; A61B 17/1757; A61B 17/1764

USPC .................................. 606/86 R, 87, 96, 97
See application file for complete search history.

(56) References Cited

U.S. PATENT DOCUMENTS

| | | | |
|---|---|---|---|
| 6,711,432 B1 * | 3/2004 | Krause | A61B 90/36 600/426 |
| 8,282,645 B2 | 10/2012 | Lawrence | |
| D695,402 S | 12/2013 | Dacosta | |
| 10,292,713 B2 | 5/2019 | Fallin | |
| 10,342,590 B2 | 7/2019 | Bays | |
| 10,376,268 B2 | 8/2019 | Fallin | |
| 10,561,426 B1 | 2/2020 | Dayton | |
| 10,646,263 B2 | 5/2020 | Lamm | |
| 10,849,670 B2 | 12/2020 | Santrock | |
| 10,888,335 B2 | 1/2021 | Dayton | |
| 10,898,211 B2 | 1/2021 | Fallin | |
| 10,945,764 B2 | 3/2021 | Dayton | |
| 11,058,546 B2 | 7/2021 | Hollis | |
| 11,304,705 B2 | 4/2022 | Fallin | |
| 11,304,735 B2 | 4/2022 | Sayger | |
| 11,523,845 B2 | 12/2022 | Dayton | |

(Continued)

OTHER PUBLICATIONS https://www.medetzsurgical.com/428m10/osteotomy-guide-system.html.

(Continued)

*Primary Examiner* — Marcela I. Shirsat

(57) ABSTRACT

Surgical systems and methods for performing an osteotomy are disclosed herein. A surgical system includes a frame including a first section, second section, third section, fourth section, and a window. The surgical system can include a cut guide that can fit within the window and contact the first side, the second side, the third side, and the fourth side. The surgical system can include an aligner that can fit within the window and contact the first side, the second side, the third.

20 Claims, 23 Drawing Sheets

(56) References Cited

U.S. PATENT DOCUMENTS

| | | | |
|---|---|---|---|
| 11,547,425 B1* | 1/2023 | Lebrija | A61B 17/66 |
| 2007/0265634 A1 | 11/2007 | Weinstein | |
| 2008/0172056 A1* | 7/2008 | Edwards | A61B 90/92 |
| | | | 606/104 |
| 2009/0198244 A1* | 8/2009 | Leibel | A61B 17/1782 |
| | | | 606/87 |
| 2010/0130981 A1* | 5/2010 | Richards | A61B 17/15 |
| | | | 606/87 |
| 2012/0303033 A1 | 11/2012 | Weiner | |
| 2014/0336658 A1* | 11/2014 | Luna | A61B 17/15 |
| | | | 606/87 |
| 2017/0042598 A1* | 2/2017 | Santrock | A61B 17/1682 |
| 2017/0042599 A1* | 2/2017 | Bays | A61B 17/8866 |
| 2017/0079669 A1 | 3/2017 | Bays | |
| 2018/0289423 A1 | 10/2018 | Singh | |
| 2019/0336140 A1 | 11/2019 | Dacosta | |
| 2021/0077192 A1* | 3/2021 | Perler | G06T 11/008 |
| 2023/0263536 A1* | 8/2023 | Kuyler | A61B 17/66 |
| | | | 606/57 |

OTHER PUBLICATIONS

Medetz Surgical Instruments: Orthopedic Surgical Instruments, Reese Osteotomy Guide https://www.medetzsurgical.com/428m10/osteotomy-guide-system.html.

* cited by examiner

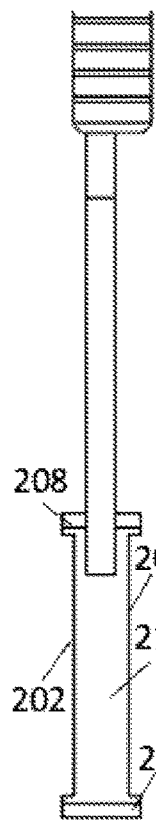
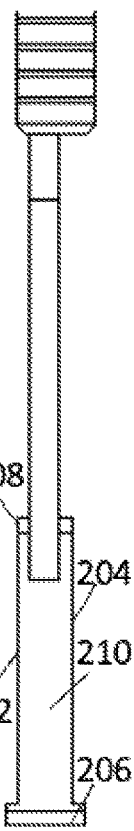
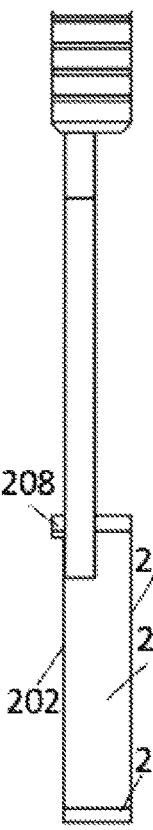
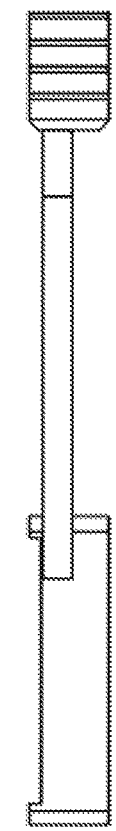
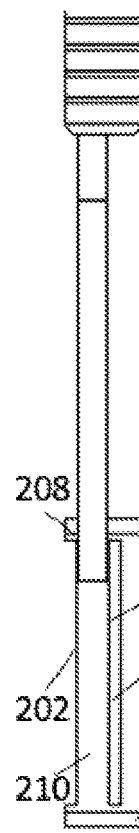
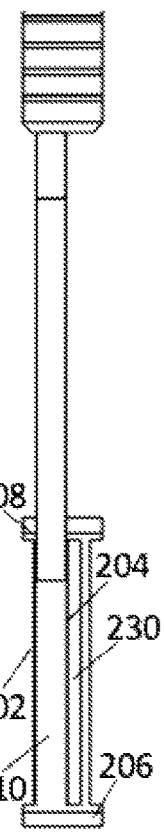
FIG. 2B   FIG. 2C   FIG. 2D   FIG. 2E   FIG. 2F   FIG. 2G
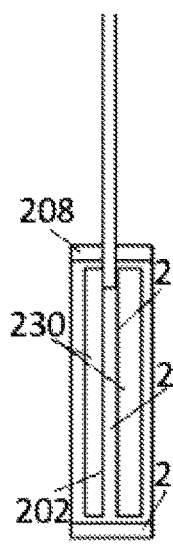
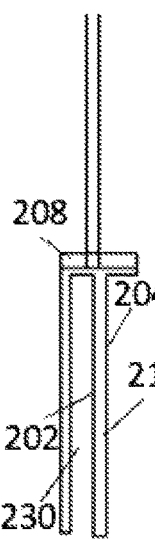
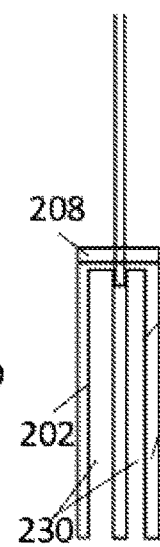
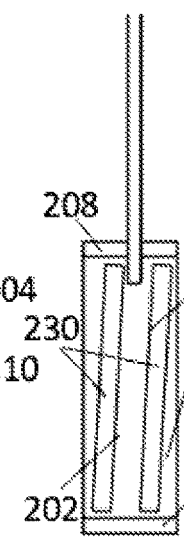
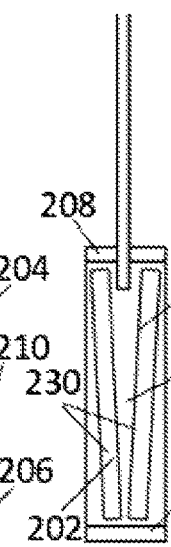
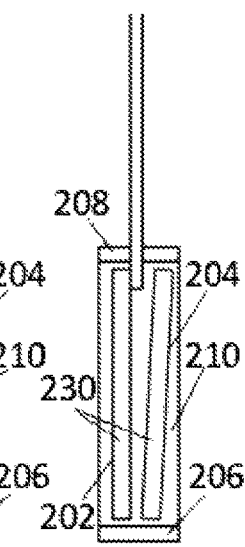
FIG. 2H   FIG. 2I   FIG. 2J   FIG. 2K   FIG. 2L   FIG. 2M

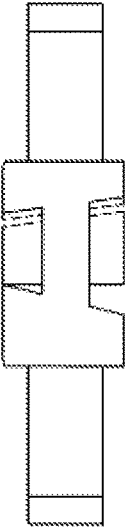
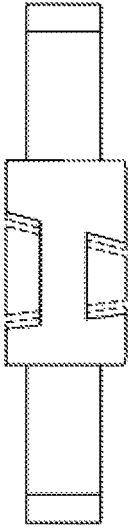
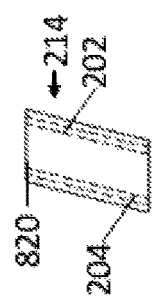
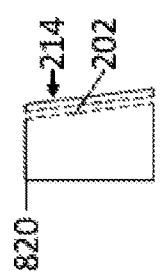
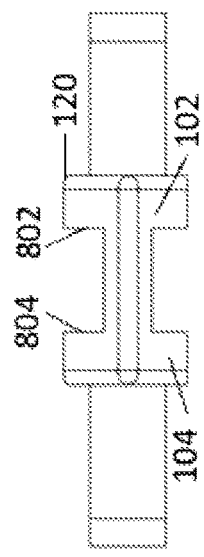
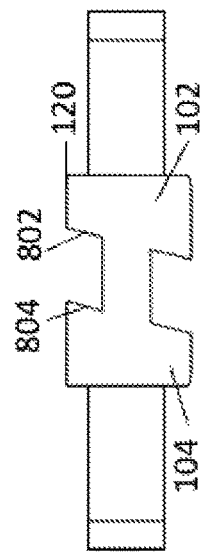
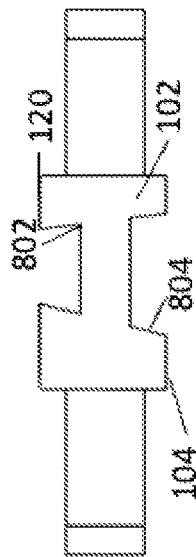

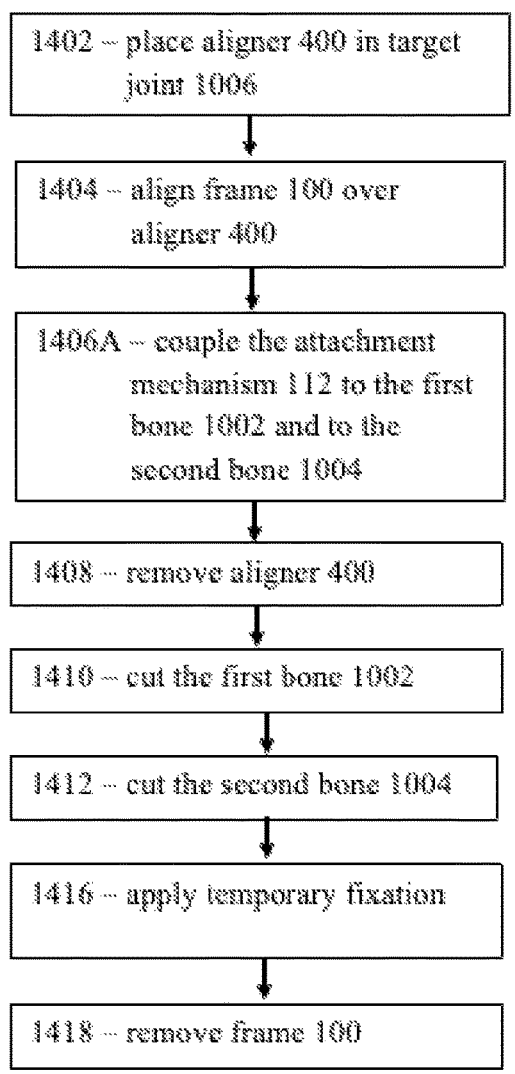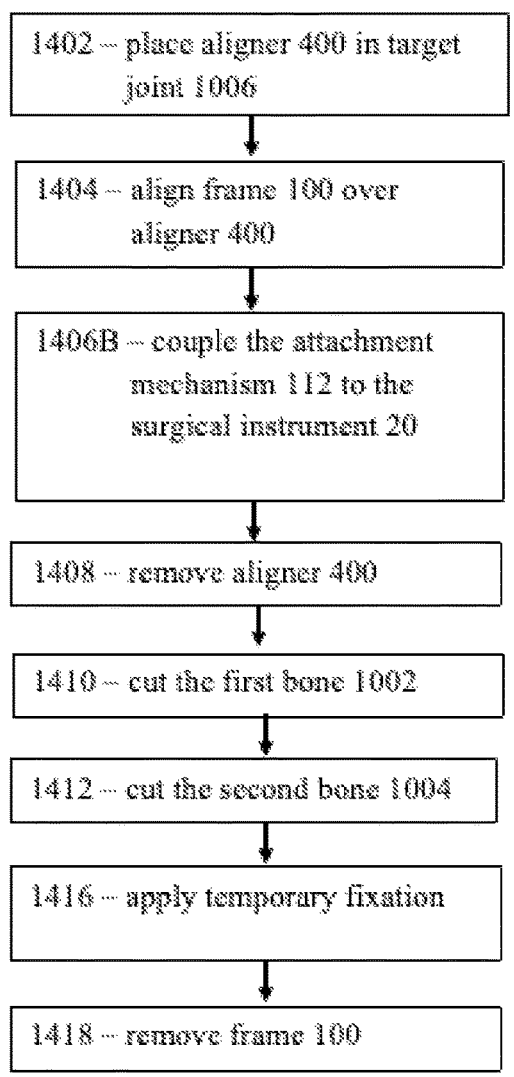

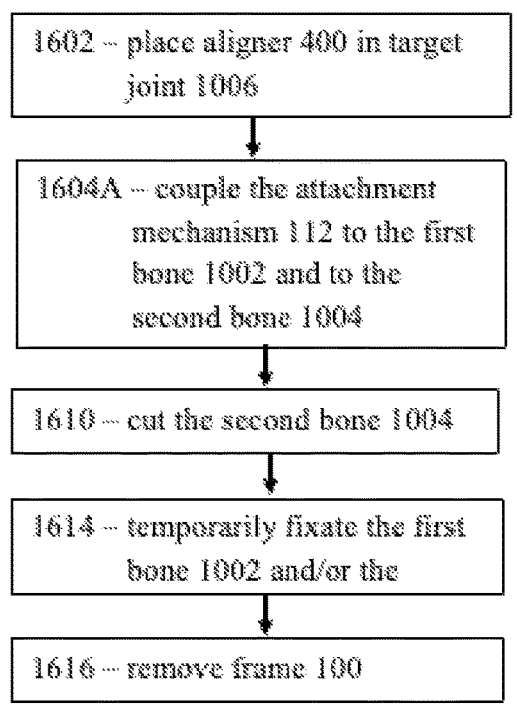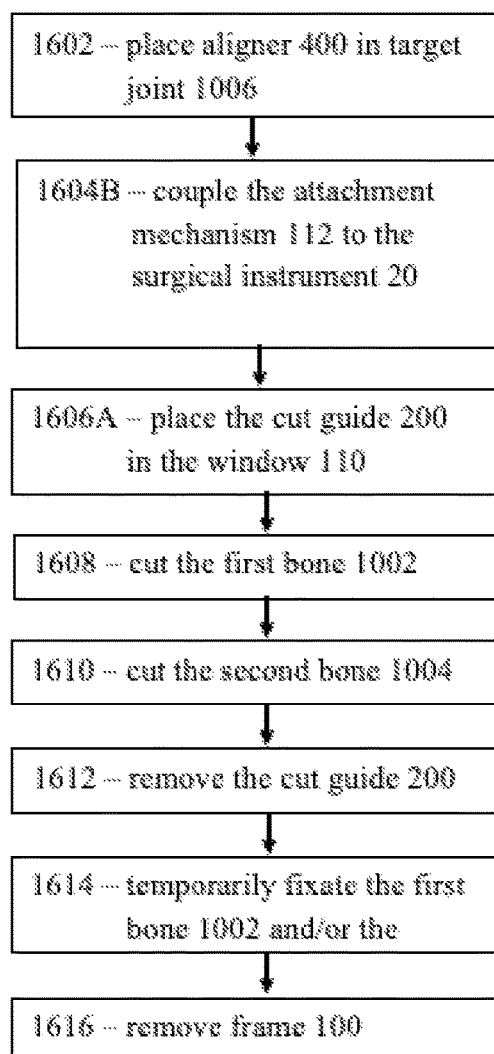

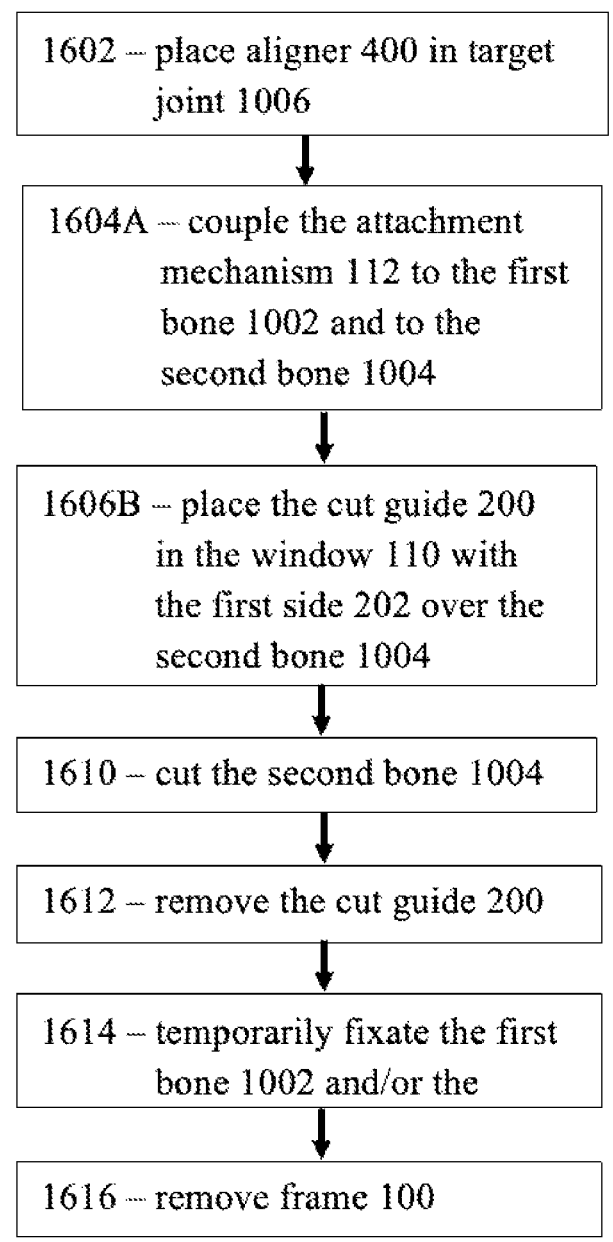

SURGICAL SYSTEMS AND METHODS INCLUDING CUTTING AND ALIGNING GUIDES FOR PERFORMING AN OSTEOTOMY

FIELD OF THE TECHNOLOGY

The present technology relates generally to surgical cutting and aligning guides, and more particularly to, surgical instruments and systems for performing an osteotomy.

BACKGROUND

Surgical cut guides can be helpful in performing an osteotomy. However, they can be difficult to align properly and can restrict visibility of and access to the osteotomy site. This restriction can require multiple installations and removals of a cutting and/or aligning guide which can add time to the surgical procedure and add damage to a patient's bone. The goal in an osteotomy is often to remove as little bone as possible to prevent negative surgical outcomes. Some cut guides only allow for a fixed amount of bone removal, which may or may not be ideal for a specific patient.

SUMMARY

A surgical system comprising a first section, a second section, a third section and a fourth section, which define a window. The first section and the second section can be separated by a first width. The first section is configured to align with a first bone. The second section is configured to align with a second bone. The window includes a size that is configured to span a target joint between the first and second bones when the first section is aligned with the first bone and the second section is aligned with the second bone to provide surgical access to the target joint. The surgical system can further comprise at least one attachment mechanism that can be coupled to at least one of the first section, the second section, the third section, and the fourth section. The attachment mechanism can be configured to secure the surgical system to the first bone, the second bone, and/or a surgical jig.

The surgical system can further comprise a cut guide. The cut guide can comprise a head. The head can comprise a first member and a second member. The first member can be perpendicular to the second member. The head can further comprise a third member that can be parallel to the first member and perpendicular to the second member. The first member can comprise a second width. The second width can be less than the first width which allows the head to fit within the window and contact the first section, the second section, the third section, and the fourth section. The second member can comprise a fourth width that is less than the second width and is centered within the second width. The cut guide can further comprise a placement device that can be comprised of at least one of a handle, a handlebar, a magnet, a bar, a knob, a hold, a grip, a shaft, and a tab.

The surgical system can further comprise an aligner. The aligner can be detachable. The aligner can comprise a grip. The grip can comprise a grip depth that is less than the first width such that the grip fits within the window and contacts the first section, the second section, the third section, and the fourth section. The grip can at least partially comprise a high friction surface. The aligner can further comprise a shim. The shim can comprise a shim depth that is less than or equal to the grip depth. The shim depth can be uniform or at least partially tapered. The shim can be centered or off centered on the grip.

BRIEF DESCRIPTION OF THE DRAWINGS

To readily understand the advantages and benefits of the technology, a more particular description of the technology briefly described above will be rendered by reference to specific embodiments that are illustrated in the appended drawings. Understanding that these drawings depict typical embodiments of the technology, and are therefore not to be considered to be limiting of its scope, the technology will be described and explained with additional specificity and detail through the use of the accompanying drawings, in which:

FIGS. 2B through 2M are top views of schematic diagrams illustrating various embodiments of the surgical system including the cut guide;

FIGS. 8A through 8D are the front view of schematic diagrams illustrating various embodiments of the frame;

FIGS. 8E through 8G are the front view of schematic diagrams illustrating various embodiments of the cut guide;

FIGS. 8H through 8J are the front view of schematic diagrams illustrating various embodiments of the surgical system including the frame, and the cut guide;

FIGS. 14A through 14B are flow charts illustrating embodiments of performing an osteotomy with the frame and the aligner;

FIGS. 16A through 16C are flow charts illustrating embodiments of performing an osteotomy with the frame with an aligner.

DETAILED DESCRIPTION OF THE DRAWINGS

Figure 1A:
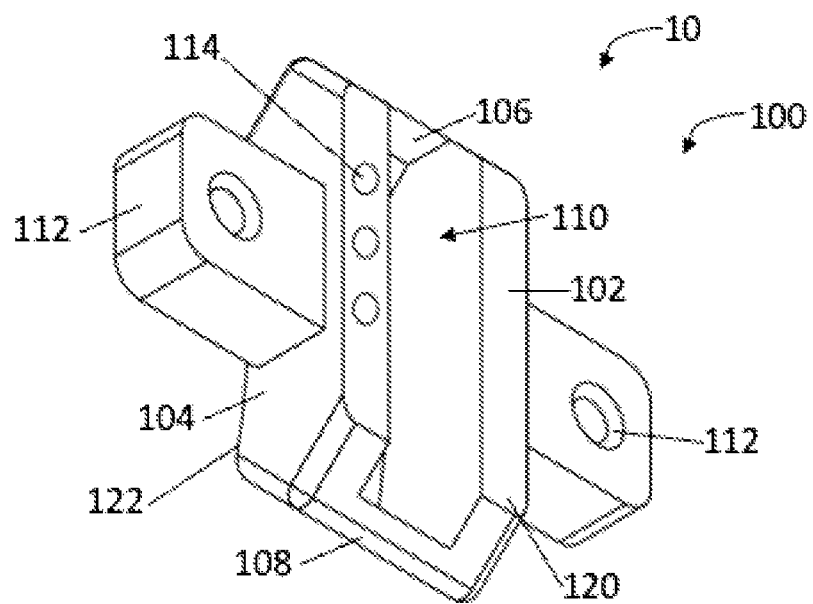
FIG. 1A is an isometric view of a schematic diagram illustrating an embodiment of a surgical system including a frame.
Figure 1B:
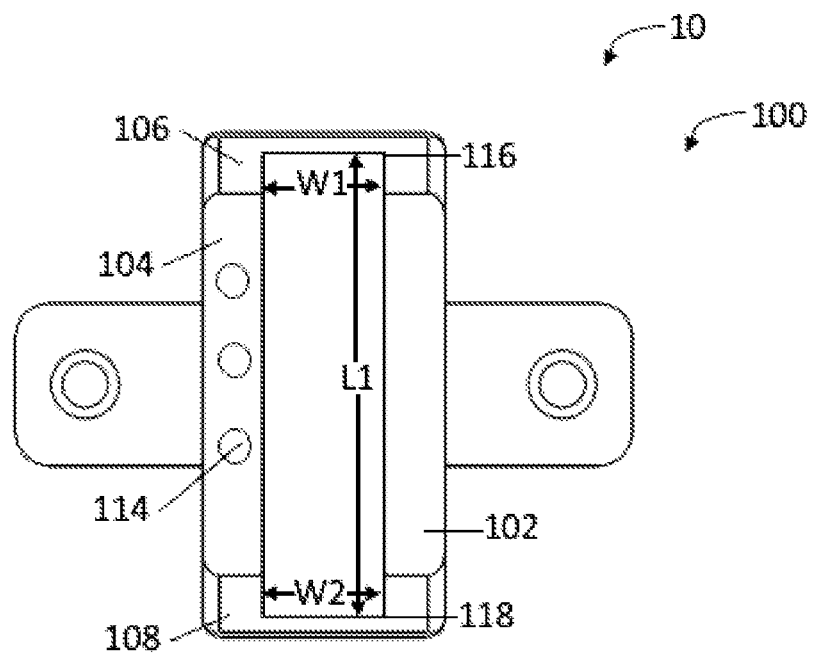
FIG. 1B is a top view of a schematic diagram illustrating an embodiment of the surgical system including the frame.
Figure 1C:
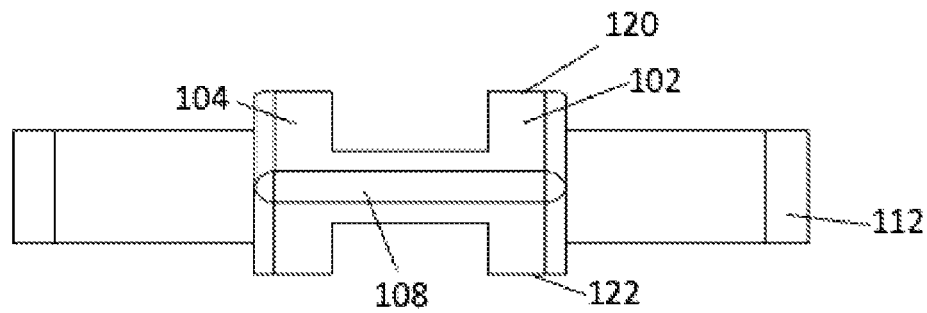
FIG. 1C is a front view of a schematic diagram illustrating an embodiment of the surgical system including the frame.
Figure 1D:
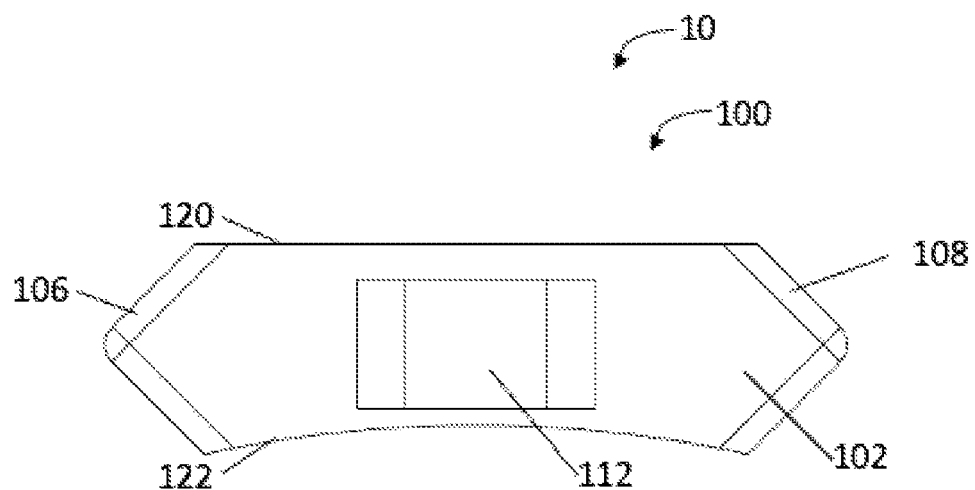
FIG. 1D is a side view of a schematic diagram illustrating an embodiment of the surgical system including the frame.
Figure 1E:
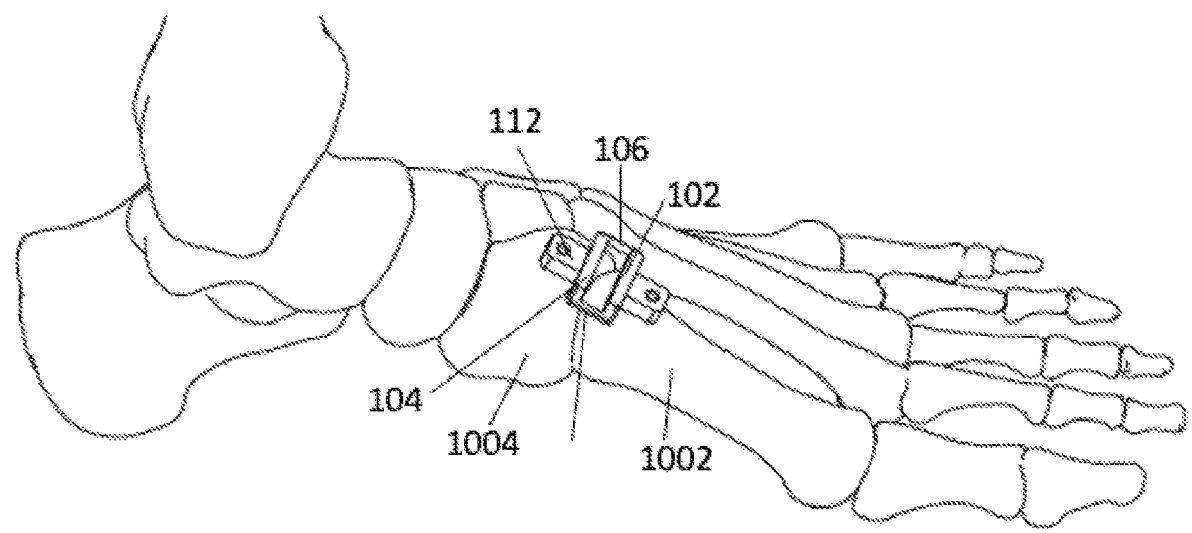
FIGS. 1E through 1H are a schematic diagrams illustrating various embodiments of the surgical system including the frame.
Figure 1F:
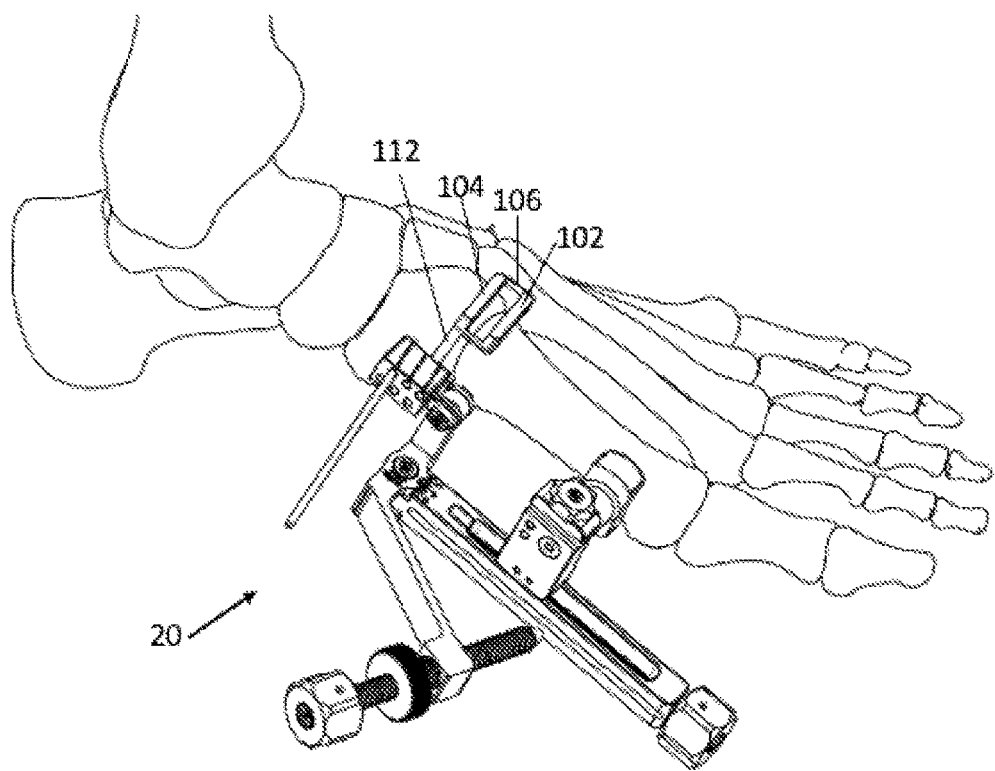
Figure 1G:
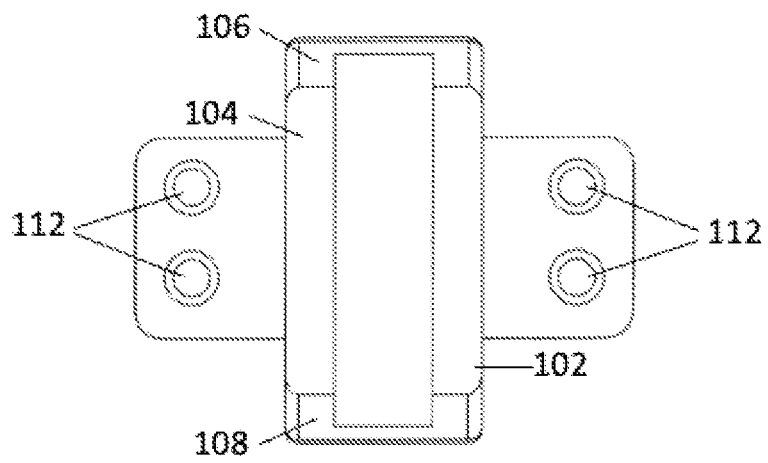
Figure 1H:
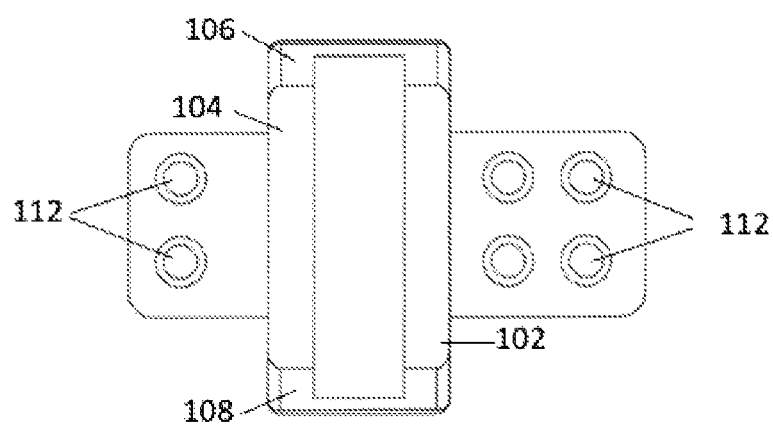
Figure 2A:
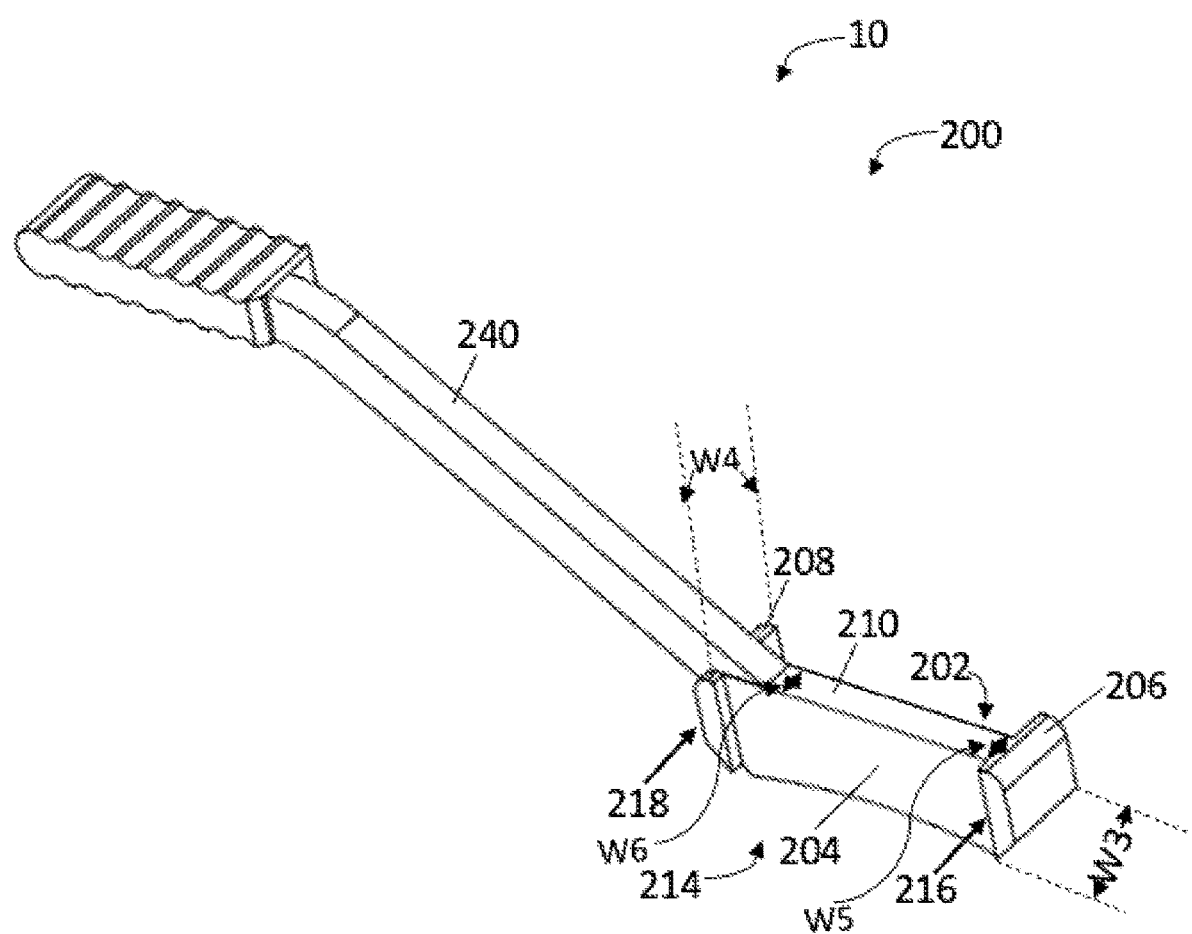
FIG. 2A is a schematic diagram illustrating an embodiment of the surgical system including a cut guide.

It should be understood that the language used in the present disclosure has been principally selected for readability and instructional purposes, and not to limit the scope of the subject matter disclosed herein in any manner. Further, reference throughout this specification to "one embodiment," "an embodiment," or similar language means that a particular feature, structure, or characteristic described in connection with the embodiment is included in at least one embodiment. Thus, appearances of the phrases "in one embodiment," "in an embodiment," and similar language throughout this specification may, but do not necessarily, all refer to the same embodiment, but mean "one or more but not all embodiments" unless expressly specified otherwise. The terms "including," "comprising," "having," and variations thereof mean "including, but not limited to" unless expressly specified otherwise. An enumerated listing of items does not imply that any or all of the items are mutually exclusive and/or mutually inclusive, unless expressly specified otherwise. The terms "a," "an," and "the" also refer to "one or more" unless expressly specified otherwise.

In addition, as used herein, the term "set" can mean "one or more," unless expressly specified otherwise. The term "sets" can mean multiples of or a plurality of "one or mores," "ones or more," and/or "ones or mores" consistent with set theory, unless expressly specified otherwise.

In addition, as used herein, the term "first bone" can refer to a bone or bone portion. The term "second bone" can refer to a bone that is a different bone than the first bone, or it can refer to a separate portion of the same bone as the first bone. The term "joint" can refer to the place where two bones meet, and/or the ends of those bones, such as in the case of the first bone and the second bone being different bones. The term "joint" can refer to a fracture, such as in the case where "first bone" refers to a first bone portion and "second bone" refers to a different portion of the same bone. The term "joint" can also refer to the desired location of an osteotomy.

Furthermore, the described features, advantages, and characteristics of the embodiments may be combined in any suitable manner. One skilled in the relevant art will recognize that the embodiments may be practiced without one or more of the specific features or advantages of a particular embodiment. In other instances, additional features and advantages may be recognized in certain embodiments that may not be present in all embodiments. Aspects of the embodiments are described below with reference to schematic flowchart diagrams and/or schematic block diagrams of methods, apparatuses, and systems according to embodiments. The schematic flowchart diagrams and/or schematic block diagrams in the Figures illustrate the structure, functionality, and operation of possible implementations of apparatuses, systems, and methods according to various embodiments.

It should also be noted that, in some alternative implementations, the functions noted in the block may occur out of the order noted in the Figures. For example, two blocks shown in succession may, in fact, be executed substantially concurrently, or the blocks may sometimes be executed in the reverse order. Other steps and methods may be conceived that are equivalent in function, logic, or effect to one or more blocks, or portions thereof, of the illustrated Figures.

Although various arrow types and line types may be employed in the flowchart and/or block diagrams, they are understood not to limit the scope of the corresponding embodiments. Indeed, some arrows or other connectors may be used to indicate only the logical flow of the depicted embodiment. For instance, an arrow may indicate a waiting or monitoring period of unspecified duration between enumerated steps of the depicted embodiment. It will also be noted that each block of the block diagrams and/or flowchart diagrams, and combinations of blocks in the block diagrams and/or flowchart diagrams, can be implemented by special purpose hardware-based systems that perform the specified functions or acts, or combinations of special purpose hardware and code.

The present technology may include any type of surgical system and is not limited to the style of surgical system depicted in the drawings. Furthermore, the described features, structures, or characteristics of the various embodiments may be combined in any suitable manner. One skilled in the relevant art will recognize, however, that embodiments may be practiced without one or more of the specific details, or with other methods, components, materials, and so forth. In other instances, well-known structures, and/or materials are not shown or described in detail to avoid obscuring aspects of an embodiment.

Turning now to the Figures, FIGS. 1A through 9C are schematic diagrams illustrating various views and/or embodiments of a surgical system 10. In various embodiments, the surgical system 10 can be utilized to perform a wedge-shaped osteotomy, straight-cut osteotomy, and/or parallel-cut osteotomy.

The surgical system 10 may be constructed of any suitable material. In various embodiments, the surgical system 10 is constructed of a sterilized suitable material. In some embodiments, the surgical system 10 includes stainless steel, radio-opaque, titanium, titanium alloy, and/or aluminum, among other suitable materials that are possible and contemplated herein. In additional or alternative embodiments, the surgical system 10 includes surgical grade stainless steel, among other suitable surgical grade materials that are possible and contemplated herein.

Referring now to FIGS. 1A through 1H. At least in the illustrated embodiment, the surgical system 10 includes, among other features, a frame 100. The frame 100 includes, among other features a first section 102, a second section 104, a third section 106, and a fourth section 108 which form a window 110 therebetween. The window includes a window first end 116 with a first window width W1 and a window second end 118 with a second window width W2. The frame 100 and/or window 110 may include any suitable dimensions that can assist in performing an osteotomy. In various embodiments, the frame 100 and/or window 110 includes dimensions that are suitable for performing an osteotomy on a human. In various embodiments, the frame 100 and/or window 110 includes dimensions that are suitable for performing a Lapidus procedure, a metadductus procedure, and/or metatarsus adductus, talar-navicular fusion, calcaneal cuboid fusion, shortening osteotomies, among other procedures that are possible and contemplated herein.

The first window width W1 and the second window width W2 can be equal wherein the first section 102 and the second section 104 can be parallel and separated by the width W 1. In some embodiments the first window width W1 can be greater than the second window width W2. In other embodiments the second window width W2 can be greater than the first window width W 1. In some embodiments the width W1 can be in the range of 4 mm to 12 mm, among other ranges that are suitable and contemplated herein. In some embodiments the width W1 is about 6 mm. In some embodiments the width W1 is greater than 6 mm, and in other embodiments the width W1 is less than 6 mm. In some embodiments the second window width W2 can be in the range of 4 mm to 12 mm, among other ranges that are suitable and contemplated herein. In some embodiments the second window width W2 is about 6 mm. In some embodiments the second window width W2 is greater than 6 mm, and in other embodiments the second window width W2 is less than 6 mm.

The third section 106 and the fourth section 108 can be parallel and separated by a length L1. The length L1 can be in the range of 18 mm to 23 mm, among other ranges that are suitable and contemplated herein. In some embodiments the length L1 is about 21 mm. In some embodiments the length L1 can be greater than 21 mm, and in other embodiments the length L1 can be less than 21 mm.

In various embodiments the first section 102, the second section 104, the third section 106, and/or the fourth section 108 can be contoured to conform to the shape of a bone (e.g., see FIG. 1D), for example, a metatarsal, a cuneiform, talus, navicular, cuboid, and/or calcaneus, among other shapes that are possible and contemplated herein. In various embodiments a frame top 120 and a frame bottom 122 are the same shape so as to be reversible. In various embodiments the frame top 120 and the frame bottom 122 are different shapes which may assist in proper placement and/or alignment of the frame 100.

The frame 100 can include an attachment mechanism 112 which can be coupled to at least one of the first section 102, the second section 104, the third section 106, and/or the fourth section 108. In some embodiments the attachment mechanism 112 is configured to couple the frame 100 to a first bone 1002 and/or a second bone 1004 (e.g., see FIG. 1E). In some embodiments the attachment mechanism 112 is configured to couple the frame 100 to a surgical instrument 20 (e.g., see FIG. 1F), such as a surgical jig, a bone positioner, a clamp, and/or a bone positioning device, among other instruments that are possible and contemplated herein. The attachment mechanism 112 can include a platform, an aperture, a slot, a clamp, a pin, a k-wire, an olive wire, and/or a detent, among other devices that are possible and contemplated herein.

The frame 100 can include a radiograph positioning tool 114. The radiograph positioning tool 114 can be one or more apertures, a fin, and/or extension among other tools that are possible and contemplated herein. At least one aperture can be through at least one portion of the frame 100, such as, the first section 102, the second section 104, the third section 106, the fourth section 108, and/or the attachment mechanism 112, among other portions that are possible and contemplated herein. The aperture can be any shape, such as, a smiley face, text, circular, square, among other shapes that are possible and contemplated herein.

Referring now to FIGS. 2A through 2M. the surgical system 10 can include, among other features, a cut guide 200. The cut guide 200 can include, among other features, a head 214. The head 214 can include a first end 216 with a first head width W3 and a second end 218 with a second head width W4. The first head width W3 can be the same as, or different from, the second head width W4. In some embodiments the first head width W3 is greater than the second head width W4. In other embodiments the first head width W3 is less than the second head width W4. In some embodiments the first head width W3 can be in the range of 4 mm to 12 mm, among other ranges that are suitable and contemplated herein. In some embodiments the width first head width W3 is about 6 mm. In some embodiments the first head width W3 is greater than 6 mm, and in other embodiments the first head width W3 is less than 6 mm. In some embodiments the second head width W4 can be in the range of 4 mm to 12 mm, among other ranges that are suitable and contemplated herein. In some embodiments the second head width W4 is about 6 mm. In some embodiments the second head width W4 is greater than 6 mm, and in other embodiments the second head width W4 is less than 6 mm.

In various embodiments the head 214 can comprise a first end member 206 at the first end 216 and a middle member 210 coupled to, or integral with, the first end member 206. The first end member 206 and the middle member 210 can be of any shape and/or size suitable to perform an osteotomy, such as, a wedge-shaped osteotomy, straight-cut osteotomy, and/or parallel-cut osteotomy. The head 214 can further include a cut guide first side 202 and a cut guide second side 204.

In various embodiments, the head 214 can include a second end member 208 at the second end 218. The middle member 210 can be coupled to or integral with the second end member 208. The middle member 210 can have a first width W5 proximal to the first end member 206 and a second width W6 that is proximal to the second end member 208. In some embodiments the first width W5 can be the same as the second width W6. In other embodiments the first width W5 is greater than the second width W6. In other embodiments the first width W5 is less than the second width W6. The first width W5 can be less than or equal to the first head width W3. The second width W6 can be less than or equal to the second head width W4.

The middle member 210 can have one or more slot(s) 230 formed through it. The one or more slots can be parallel or angled relative to each other. At least one slot 230 can be perpendicular relative to the first end member 206 (e.g., see FIGS. 2F, 2G, 2H, 2I, 2J), or it can be angled relative to the first end member (e.g., see FIGS. 2K, 2L, 2M). The slot(s) 230 can be of any suitable shape and/or size to receive a cutting instrument 1008 (FIG. 10E) suitable to perform an osteotomy, such as, a wedge-shaped osteotomy, straight-cut osteotomy, and/or parallel-cut osteotomy.

The cut guide 200 can include a placement device 240. The placement device 240 can comprise at least one of a handle, a handlebar, a magnet, a bar, a knob, a hold, a grip, a shaft, a tab, a ring, a pull, among other devices that are possible and contemplated herein.

Figure 3B:
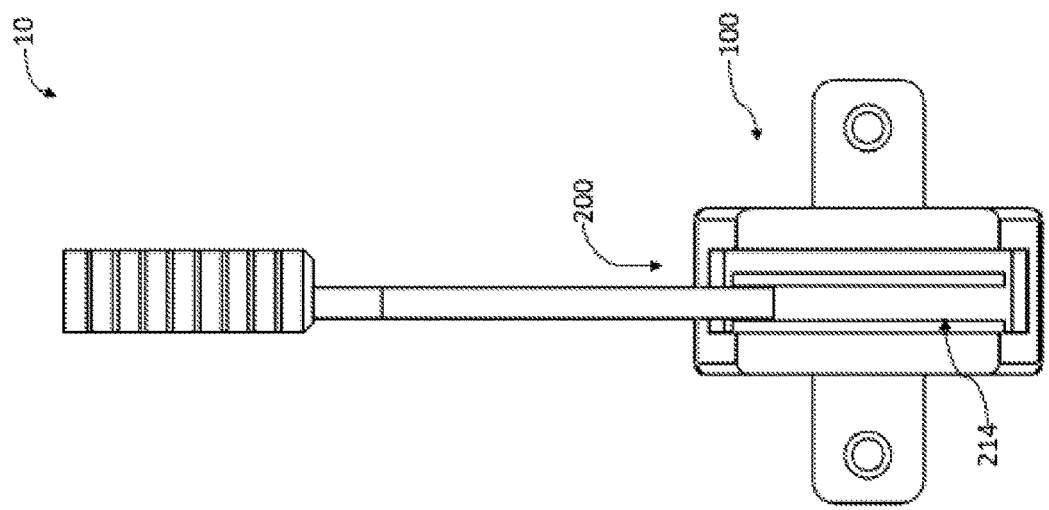
FIGS. 3A through 3B are schematic diagrams illustrating various embodiments of the surgical system including the cut guide inserted into the frame.
Figure 3A:
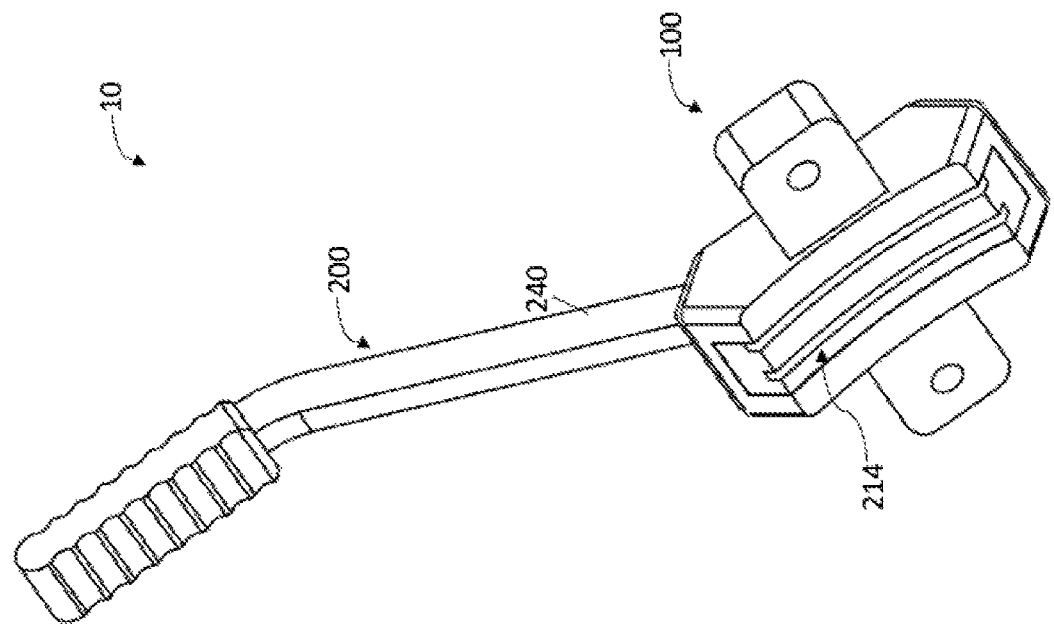

Turning now to FIGS. 3A and 3B. In various embodiments the first head width W3 and the second head width W4 are slightly less than the first window width W1 and the second window width W2 respectively, such that the head 214 can fit within the window 110 and make contact with at least a portion of the first section 102, the second section 104, the third section 106, and the fourth section 108.

Figure 4C:
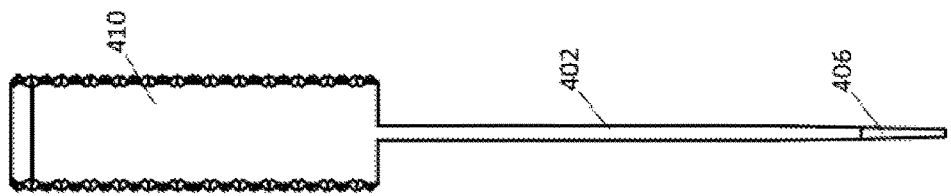
FIGS. 4A through 4C are schematic diagrams illustrating various embodiments of the surgical system including an aligner.
Figure 4B:
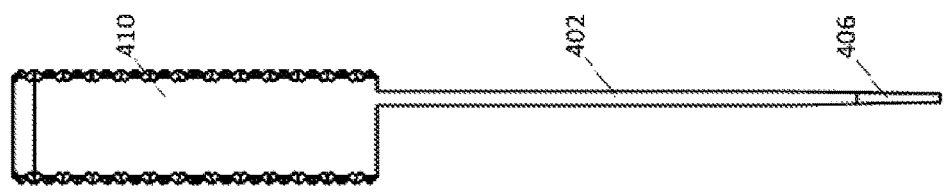
Figure 4A:
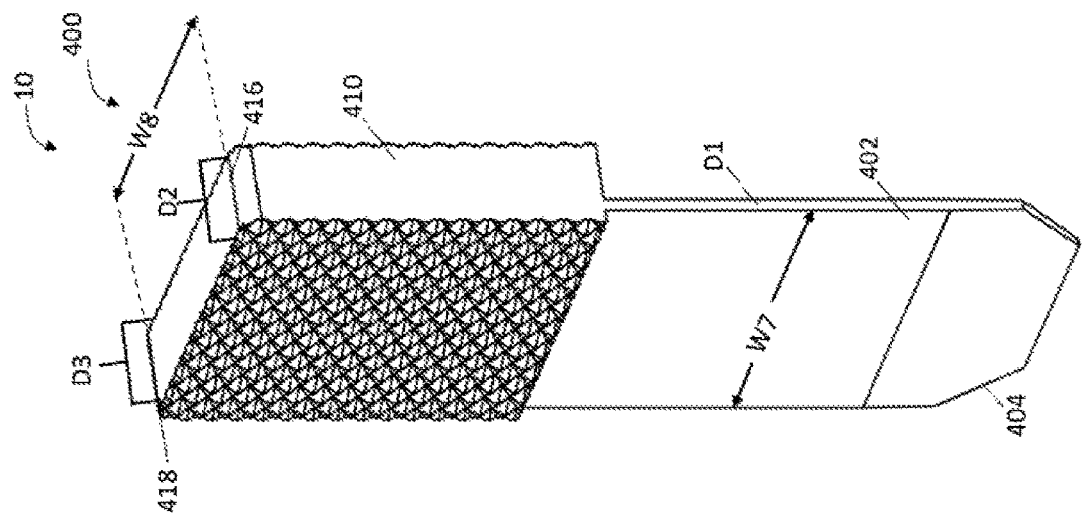
Figure 6B:
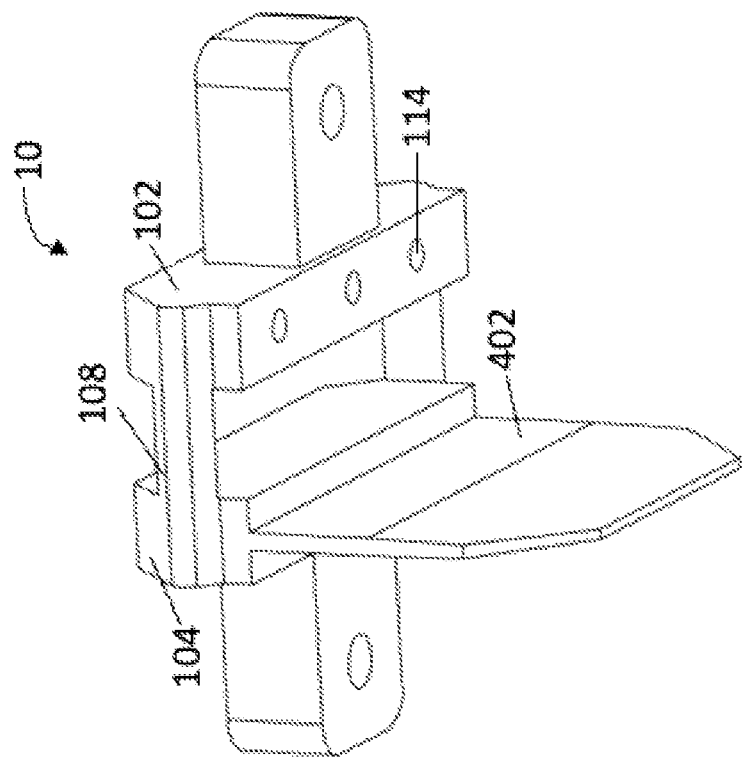
FIGS. 6A through 6B are schematic diagrams illustrating various embodiments of the surgical system including the frame and an integral aligner.
Figure 6A:
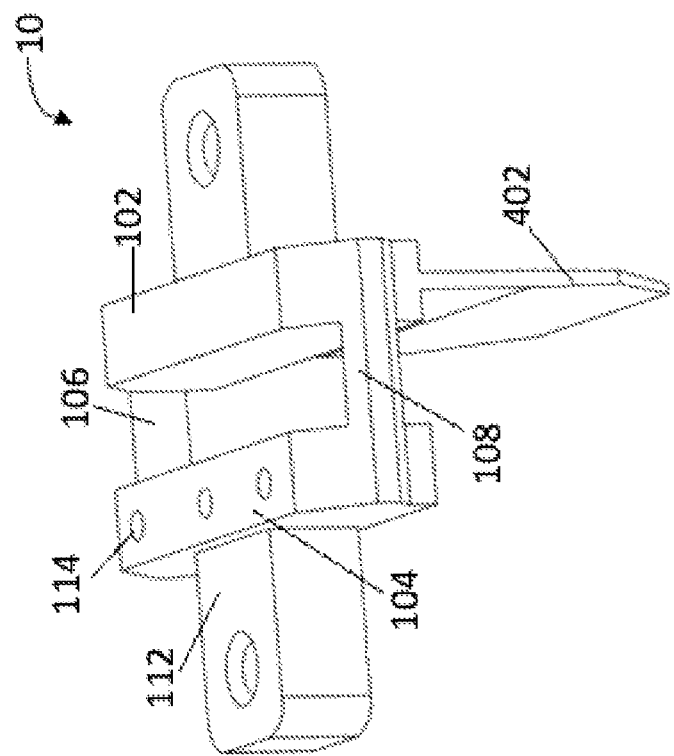

Referring to FIGS. 4A through 4C. The surgical system 10 can include an aligner 400. The aligner 400 can include a shim 402. The shim 402 can have any size and/or shape suitable to assist in performing an osteotomy, such as a wedge-shaped osteotomy, straight-cut osteotomy, and/or parallel-cut osteotomy. The shim 402 can have a shim width W7. The shim width can be uniform, tapered (404), and/or curved, among other shapes that are possible and contemplated herein. The shim can have a shim depth D1 which can be uniform, and/or tapered (406), among other shapes that are possible and contemplated herein.

The aligner 400 can further include a grip 410 with a grip width W8, a first grip depth D2 at a first grip end 416 and a second grip depth D3 at a second grip end 418. In various embodiments the first grip depth D2 can be the same as the second grip depth D3 such that the grip depth is uniform. In other embodiments the first grip depth D2 can be different from the second grip depth D3 such that the grip depth tapers. In some embodiments the first grip depth D2 can be greater than the second grip depth D3. In other embodiments the first grip depth D2 can be less than the second grip depth D3. At least a portion of the grip 410 surface can be high friction, or have a high friction coating, such as, knurling, grooves, titanium coating, stippling, among other surfaces that are possible and contemplated herein.

The shim 402 can be centered on or off-center from the first grip depth D2. The shim 402 can be centered on or off-center from the second grip depth D3. The shim 402 can be centered on (e.g., see FIG. 4C) or off-center (e.g., see FIG. 4B) from both the first grip depth D2 and the second grip depth D3.

Figure 5:
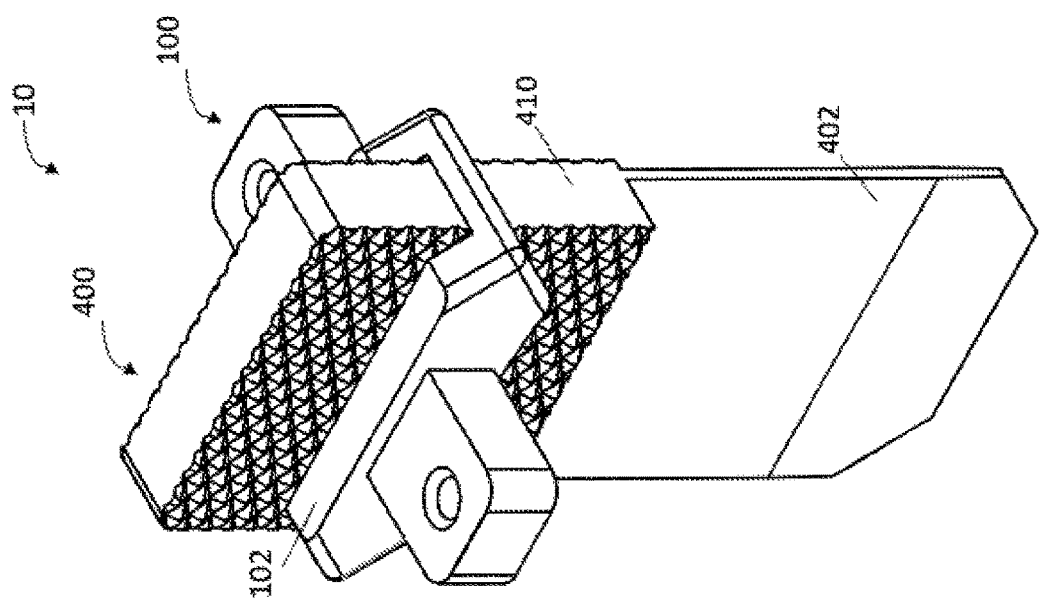
FIG. 5 is a schematic diagram illustrating an embodiment of the surgical system including the aligner inserted into an embodiment of the frame.

Referring now to FIG. 5. At least a portion of the aligner 400 can be a similar size and shape as the window 110. In various embodiments the grip 410 is a smaller size and/or shape as the window 110 such that the grip 410 can fit within the window 110 and contact at least a portion of the first section 102, the second section 104, the third section 106 and the fourth section 108. In various embodiments the first grip depth D2 is less than the first window width W1 and the second grip depth D3 is less than the second window width W2 such that the grip 410 can fit within the window 110 and contact at least a portion of the first section 102, the second section 104, the third section 106 and the fourth section 108.

In additional or alternative embodiments, the aligner 400 can be coupled to, or integral with, the first section 102 and/or the second section 104 (e.g., see FIGS. 6A and 6B) of the frame 100.

Figures 7A, 7B, 7C:
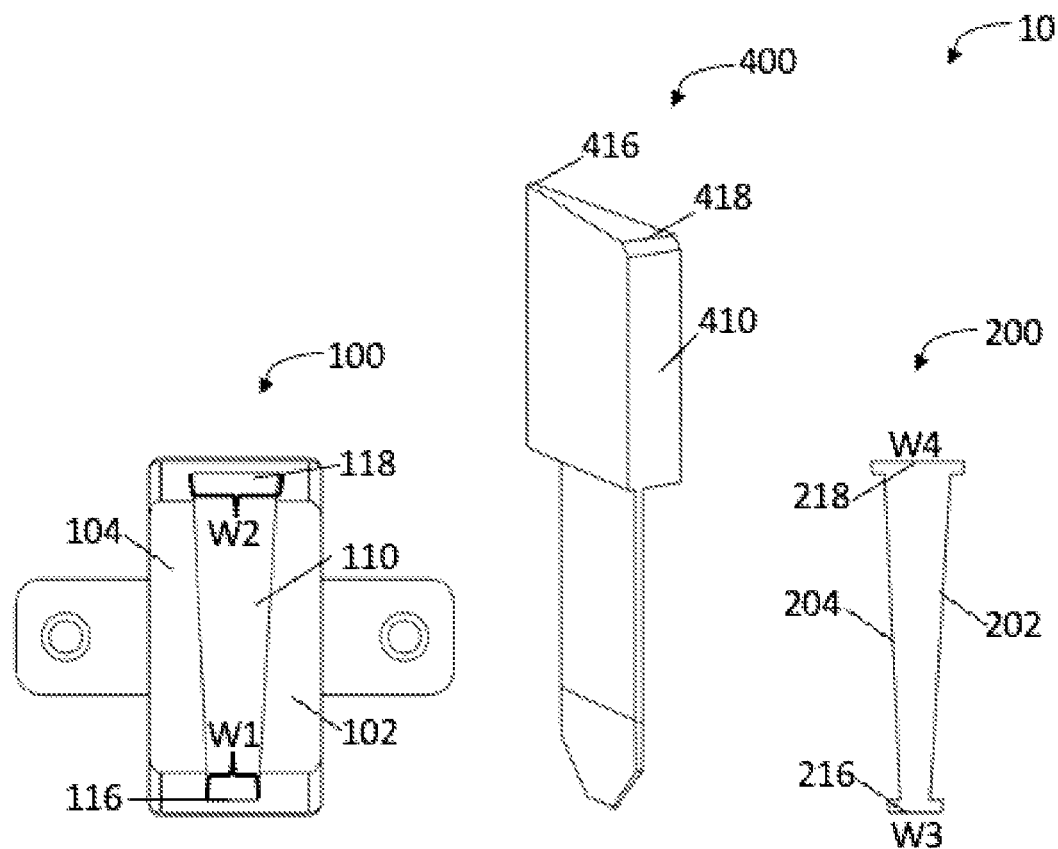
FIGS. 7A through 7E are schematic diagrams illustrating various embodiments of the surgical system including the frame, the cut guide, and/or the aligner.
Figures 7D, 7E:
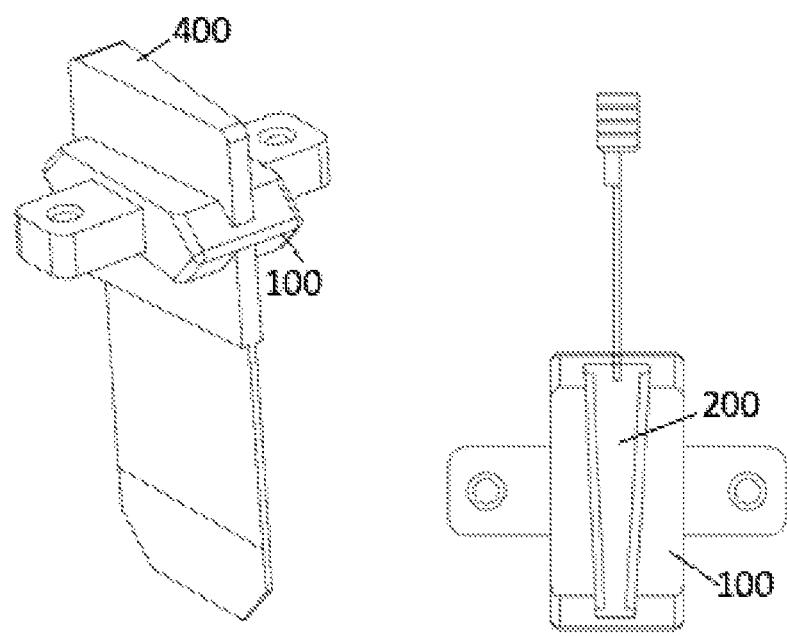
Figure 9A:
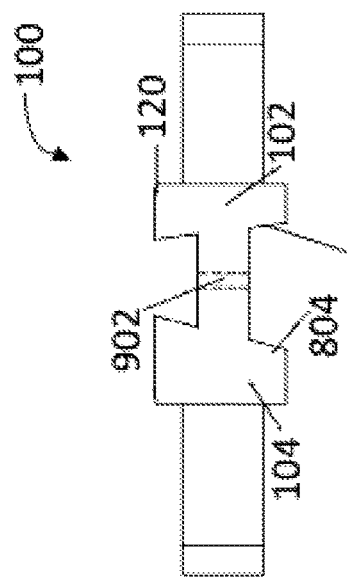
FIGS. 9A through 9D are schematic diagrams illustrating various embodiments of the surgical system including the frame and/or the aligner.
Figure 9B:
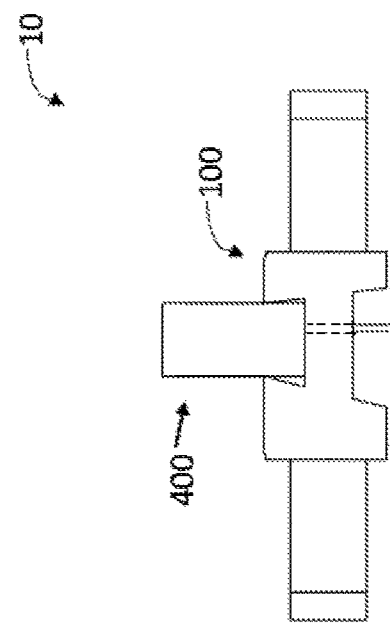
Figure 9C:
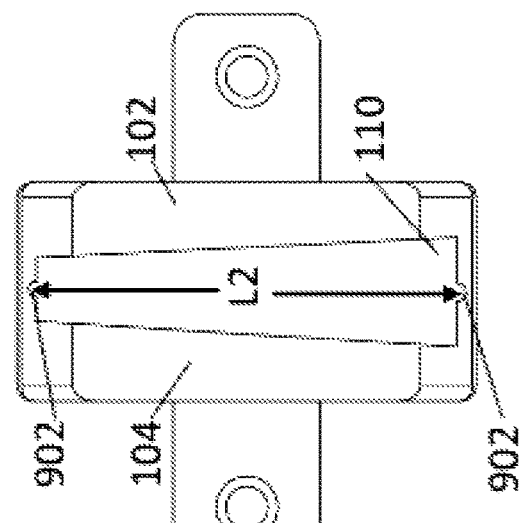
Figure 9D:
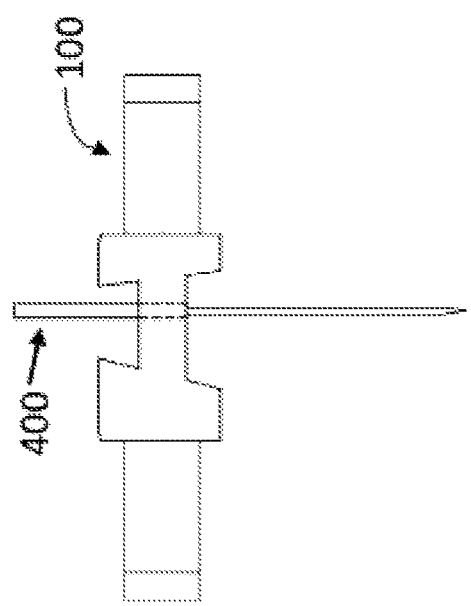

Referring now to FIGS. 7A through 7C, at least in the illustrated embodiment, surgical system 10 is comprised of the frame 100 (FIG. 7A), the cut block 200 (FIG. 7C), and the aligner 400 (FIG. 7B). The window 110, the cut block 200 head 214, and at least a portion of the aligner 400 are complimentary in size and shape. In the pictured embodiment they each taper from the second end (118, 218, and 418 respectively) to the first end (116, 216, and 416 respectively). The cut block 200 is a complimentary size and/or shape to the window 110 such that the head 214 can fit within the window. In some embodiments the head 214 can make contact with at least a portion of the first side 102, the second side 104, the third side 106, and the fourth side 108 (e.g., see FIG. 7E). The aligner 400 is a similar size and/or shape to the window 110. In some embodiments the grip 410 can fit within the window and make contact with the first side 102, the second side 104, the third side 106, and the fourth side 108 (e.g., see FIG. 7D).

Referring now to FIGS. 8A through 9C. At least in the illustrated embodiments the first section 102 can have a frame first side 802 and the second section 104 can have a frame second side 804. The frame first side 802 can be parallel with the frame second side 804 (e.g., see FIGS. 8A and 8B). The frame first side 802 can be angled relative to the frame second side 804 (e.g., see FIGS. 8C, 8D, 9B, 9C, and 9D). The frame first side 802 can be perpendicular to the frame top 120 (e.g., see FIG. 8A), or it can be angled relative to the frame top 120 (e.g., see FIGS. 8B, 8C, 8D, 8E, 9B, 9C, and 9D). The frame second side 804 can be perpendicular to the frame top 120 (e.g., see FIG. 8A), or it can be angled relative to the frame top 120. Similarly, in various embodiments, the cut guide first side 202 can be parallel with the cut guide second side 204 (e.g., see FIG. 8E). The cut guide first side 202 can be angled relative to the cut guide second side 204 (e.g., see FIGS. 8F and 8G). The cut guide first side 202 can be perpendicular to a top 820 of the cut guide 200 head 214 (e.g., see FIG. 2A), or it can be angled relative to the top 820 of the head 214 (e.g., see FIGS. 8E, 8F, and 8G). The cut guide second side 204 can be perpendicular to the top 820 of the head 214 (e.g., see FIG. 2A), or it can be angled relative to the top 820 of the head 214 (e.g., see FIGS. 8E, 8F, and 8G).

In various embodiments the window 110 can include a notch 902 on at least one of the first section 102, the second section 104, the third section 106, and/or the fourth section 108. In some embodiments the window 110 includes two notches with a notch length L2 between them. The aligner 400 and/or cut guide 200 can have complimentary bumps(s) (to fit within the notch(es), or the aligner 400 and/or cut guide 200 can be shaped to fit within the notches 902 (e.g., see FIG. 9C through 9F).

In the following examples, the first bone 1002 is cut during the method steps. This is for simplicity and ease of explanation. The first bone 1002 could be cut prior to the listed steps. This prior cut could be instead of, or in addition to, the cut during the method steps.

Figure 11A:
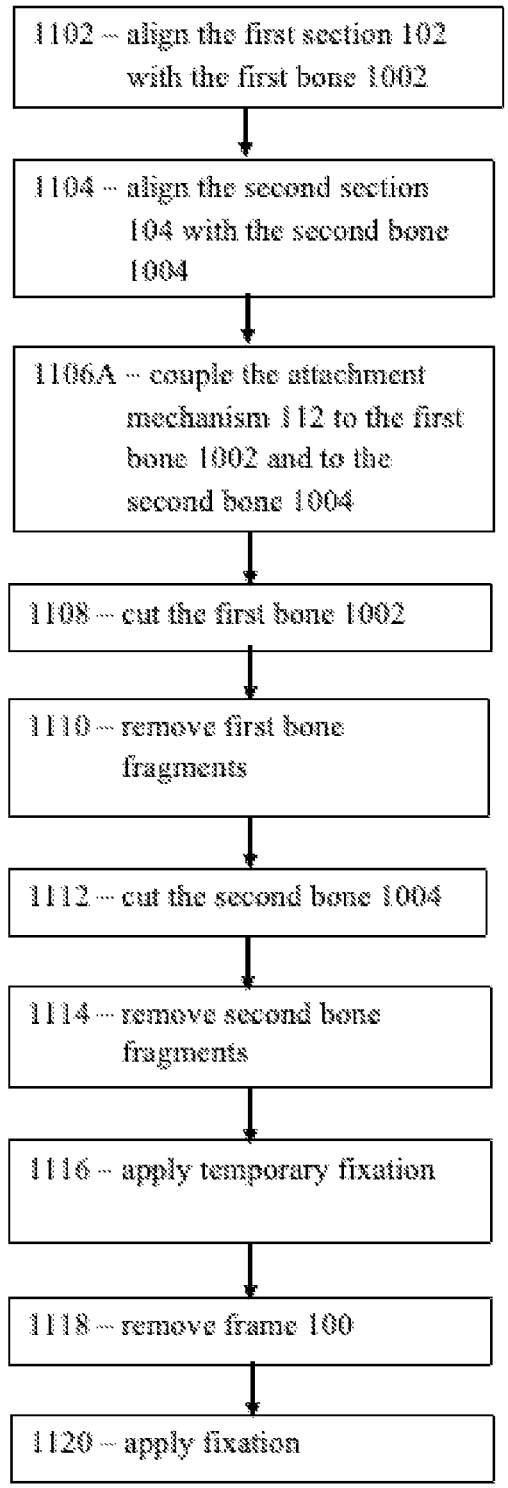
FIGS. 11A through 11B are flow charts that illustrate performing an osteotomy with the frame.

The surgical system 10 can be used in performing in a wedge-shaped osteotomy, straight-cut osteotomy, and/or parallel-cut osteotomy. The method (FIG. 11A) can include (Step 1102) Aligning the first section 102 of the frame 100 over a first bone 1002. The first bone 1002 can be any bone or portion of a bone, for example the first bone 1002 can be a cuneiform, part of a cuneiform, a metatarsal, or part of a metatarsal, a talus, part of a talus, cuboid, part of a cuboid, navicular, part of a navicular, calcaneus, or part of a calcaneus.

(Step 1104) Aligning a second bone 1004 with the second section 104 of the frame 100. The second bone 1004 can be any bone or portion of a bone, for example the second bone can be a cuneiform, part of a cuneiform, a metatarsal, or part of a metatarsal, a talus, part of a talus, cuboid, part of a cuboid, navicular, part of a navicular, calcaneus, or part of a calcaneus. The first bone 1002 is not the same as the second bone 1004.

(Step 1106A) The frame 100 can be coupled to the first bone 1002 by coupling the attachment mechanism 112 to the first bone 1002. The frame 100 can be coupled to the second bone 1004 by coupling the attachment mechanism 112 to the second bone 1004 (e.g., see FIG. 10C).

(Step 1108) The first bone 1002 can be cut by any cutting means. The first bone 1002 can be cut with a cutting instrument 1008. The cutting instrument 1008 can be at least one of any instrument capable of cutting bone, such as, a blade, a saw blade, double sided blade, a rasp, and/or an osteotome, among other instruments that are possible and contemplated herein. The cutting instrument 1008 can be held against the frame first side 802 to assist in keeping the cutting instrument 1008 straight and keep the cutting instrument 1008 from jumping or skiving and damaging the tissue surrounding the osteotomy site.

(Step 1110) If desired, bone fragments from the first bone 1002 can be removed from the osteotomy site. The bone fragments can be removed in any suitable manner. In some embodiments the bone fragments can be removed through the window 110.

(Step 1112) The second bone 1004 can be cut by any cutting means. The second bone 1004 can be cut with the cutting instrument 1008. The cutting instrument 1008 can be held against the frame second side 804 to assist in keeping the cutting instrument 1008 straight and keep the cutting instrument 1008 from jumping or skiving and damaging the tissue surrounding the osteotomy site.

(Step 1114) If desired, bone fragments from the second bone 1004 can be removed. The bone fragments can be removed in any suitable manner. In some embodiments the bone fragments can be removed through the window 110.

(Step 1116) The first bone 1002 and the second bone 1004 can be compressed together and temporary fixation applied. Temporary fixation can be any means that will keep the bones in place while their position is checked. Temporary fixation can be the placement of K-wires and/or olive pins, and/or locking of the surgical instrument 20, among other means possible and contemplated herein.

Bone positions can be checked. Checking the bone positions can include checking the position of the first bone 1002 relative to surrounding bones and/or tissues, checking the position of the second bone 1004 relative to surrounding bones and/or tissues, and checking the position of the first bone 1002 and the second bone 104 relative to each other. Bone positions can be checked using fluoroscopy, physical examination, visual examination, among other techniques that are possible and contemplated herein.

(Step 1118) The frame 100 can be removed. When using fluoroscopy, if the frame 100 is comprised of radio-opaque materials it may be removed after checking bone positions; if the frame 100 is not comprised of radio-opaque materials it may be removed before checking bone positions.

(Step 1120) Applying fixation can include applying at least one fixation device 1010 which can be anything capable of securing the bones such as, a bone plate, an intramedullary device, an intramedullary nail, a bone screw, a staple, and external fixation, among other fixation devices that are possible and contemplated herein. The at least one fixation device 1010 can be applied to the first bone 1002 and can be applied to the second bone 1004.

In additional or alternative embodiments, the method of performing an osteotomy (FIG. 11B) can include coupling the attachment mechanism 112 of the frame 100 to a surgical instrument 20 (e.g. see FIG. 1F) (step 1106B). The first bone can be cut with the cutting instrument 1008 (step 1108) (e.g., see FIG. 10E). The cutting instrument 1008 can be held against the frame first side 802 to assist in keeping the blade straight and to keep the cutting instrument from jumping or skiving and damaging bone and/or tissue near the osteotomy site.

If desired, bone fragments from the first bone 1002 can be removed from the osteotomy site (step 1110). The bone fragments can be removed in any suitable manner. In some embodiments the bone fragments can be removed through the window 110.

The second bone 1004 can be cut with the cutting instrument 1008 (step 1112). If desired, bone fragments from the second bone 1004 can be removed (step 1112). The bone fragments can be removed in any suitable manner. In some embodiments the bone fragments can be removed through the window 110.

The first bone 1002 and the second bone 1004 can be compressed together and temporary fixation applied (step 1116). Temporary fixation can be any means that will keep the bones in place while their position is checked. Temporary fixation can be the placement of K-wires and/or olive pins, locking of the surgical instrument 20, among other means possible and contemplated herein.

Bone positions can be checked. Checking the bone positions can include checking the position of the first bone 1002 relative to surrounding bones and/or tissues, checking the position of the second bone 1004 relative to surrounding bones and/or tissues, and checking the position of the first bone 1002 and the second bone 104 relative to each other. Bone positions can be checked using fluoroscopy, physical examination, visual examination, among other techniques that are possible and contemplated herein.

(Step 1118) The frame 100 can be removed. When using fluoroscopy, if the frame 100 is comprised of radio-opaque materials it may be removed after checking bone positions; if the frame 100 is not comprised of radio-opaque materials it may be removed before checking bone positions.

(Step 1120) The first bone 1002 and the second bone 1004 can be fixed by applying the fixation device 1010 to the first bone 1002 and/or to the second bone 1004.

Figure 12A:
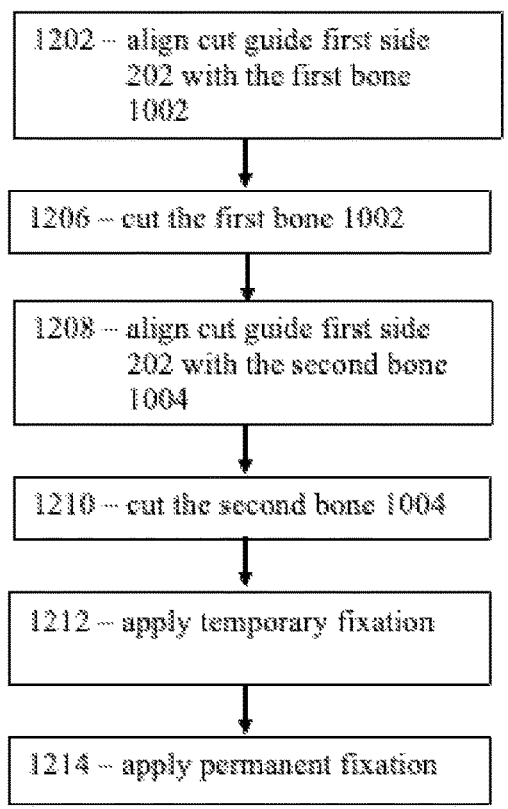
FIGS. 12A through 12B are flow charts illustrating embodiments of performing an osteotomy with the cut guide.

In additional or alternative embodiments, the method of performing an osteotomy (FIG. 12A) can include aligning the cut guide first side 202 with the first bone 1002. The first bone 1002 can be cut with the cutting instrument 1008 (step 1206). The cutting instrument 1008 can be held against the cut guide first side 202 to assist in keeping the cutting instrument 1008 straight and keep the cutting instrument 1008 from jumping or skiving and damaging bone and/or tissue near the osteotomy site. If desired, bone fragments from the first bone 1002 can be removed from the osteotomy site in any suitable manner.

The cut guide 200 can be removed, reversed, and replaced with the cut guide first side 202 aligned with the second bone 1004. The second bone 1004 can be cut with the cutting instrument 1008 (step 1210). The cutting instrument 1008 can be held against the cut guide first side 202 to assist in keeping the cutting instrument 1008 straight and to keep the cutting instrument 1008 from jumping or skiving and damaging bone and/or tissue near the osteotomy site. If desired, bone fragments from the second bone 1004 can be removed.

(Step 1212) The first bone 1002 and the second bone 1004 can be compressed together and temporary fixation applied. Temporary fixation can be any means that will keep the bones in place while their position is checked. Temporary fixation can be the placement of K-wires and/or olive pins, locking of the surgical instrument 20, among other means possible and contemplated herein.

Bone positions can be checked. Checking the bone positions can include checking the position of the first bone 1002 relative to surrounding bones and/or tissues, checking the position of the second bone 1004 relative to surrounding bones and/or tissues, and checking the position of the first bone 1002 and the second bone 104 relative to each other. Bone positions can be checked using fluoroscopy, physical examination, visual examination, among other techniques that are possible and contemplated herein.

(Step 1214) Applying fixation can include applying at least one fixation device 1010 which can be anything capable of securing the bones such as, a bone plate, an intramedullary device, an intramedullary nail, a bone screw, and/or a staple, among other fixation devices that are possible and contemplated herein. The at least one fixation device 1010 can be applied to the first bone 1002 and/or applied to the second bone 1004.

Figure 12B:
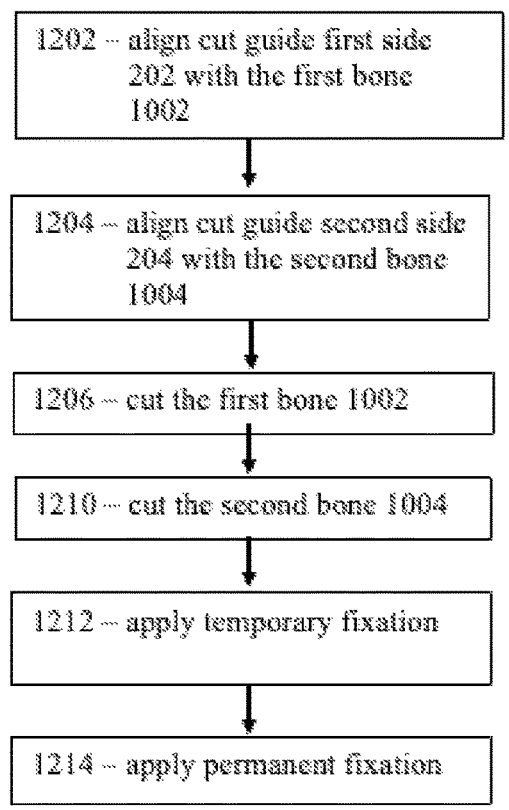

In additional or alternative embodiments, the method of performing an osteotomy (FIG. 12B) can include aligning the cut guide first side 202 with the first bone 1002 (step 1202). The first bone 1002 can be cut with the cutting instrument 1008 (step 1206). The cutting instrument 1008 can be held against the cut guide first side 202 to assist in keeping the cutting instrument straight and to keep the cutting instrument 1008 from jumping or skiving and damaging bone and/or tissue near the osteotomy site. If desired, bone fragments from the first bone 1002 can be removed from the osteotomy site.

The second bone 1004 can be cut with the cutting instrument 1008 (step 1210). The cutting instrument 1008 can be held against the cut guide second side 204 to assist in keeping the cutting instrument 1008 straight and to keep the cutting instrument 1008 from jumping or skiving and damaging bone and/or tissue near the osteotomy site. If desired, bone fragments from the second bone 1004 can be removed.

The first bone 1002 and the second bone 1004 can be compressed together and temporary fixation applied (step 1212). Temporary fixation can be any means that will keep the bones in place while their position is checked. Temporary fixation can be the placement of K-wires and/or olive pins, locking of the surgical instrument 20, among other means possible and contemplated herein.

Bone positions can be checked. Checking the bone positions can include checking the position of the first bone 1002 relative to surrounding bones and/or tissues, checking the position of the second bone 1004 relative to surrounding bones and/or tissues, and checking the position of the first bone 1002 and the second bone 104 relative to each other. Bone positions can be checked using fluoroscopy, physical examination, visual examination, among other techniques that are possible and contemplated herein.

The bones 1002 and 1004 can be fixed by applying at least one fixation device 1010 (step 1214). The at least one fixation device 1010 can be applied to the first bone 1002 and applied to the second bone 1004.

Figure 13A:
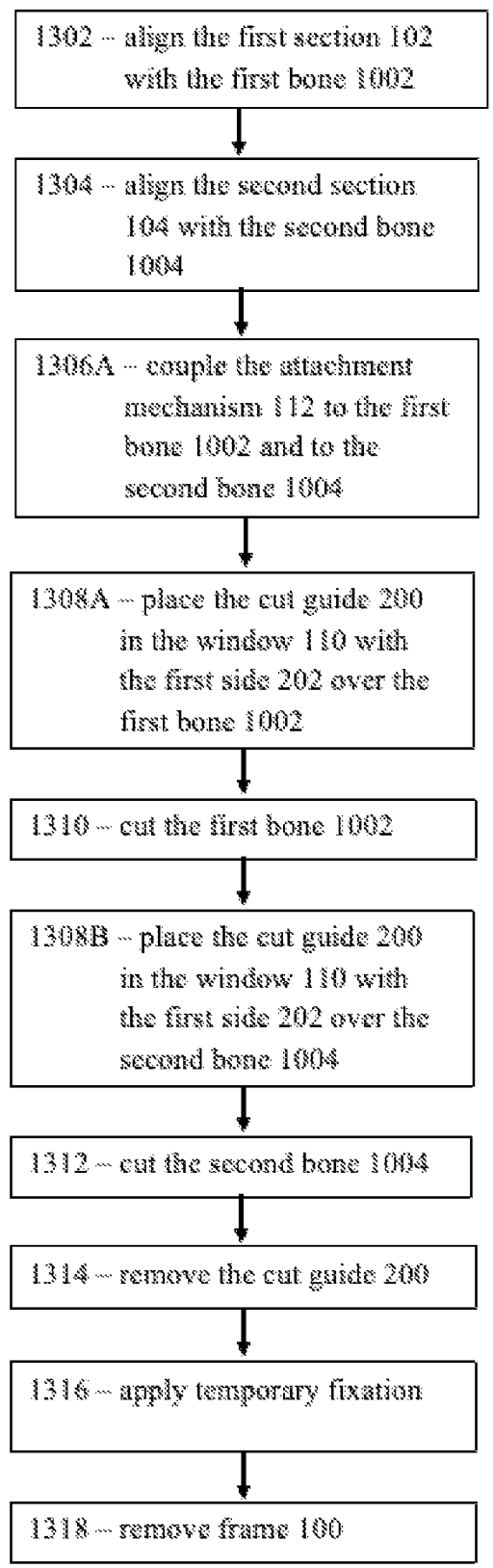
FIGS. 13A through 13C are a flow charts illustrating embodiments of performing an osteotomy with the frame and the cut guide.

In additional or alternative embodiments, the method of performing an osteotomy (FIG. 13A) can include aligning the first section 102 of the frame 100 over the first bone 1002 (step 1302). The second bone 1004 can be aligned with the second section 104 of the frame 100 (step 1304). The frame 100 can be coupled to the first bone 1002 by coupling the attachment mechanism 112 to the first bone 1002. The frame 100 can be coupled to the second bone 1004 by coupling the attachment mechanism 112 to the second bone 1004. (Step 1306A) (e.g. see FIG. 10C).

The cut guide 200 can be placed in the window 110 (step 1308A). The head 214 can be oriented within the frame 100 so that the cut guide first side 202 is over the first bone 1002 (e.g., see FIG. 10D). In some embodiments the cut guide can be selected from a kit of cut guides.

Figure 10A:
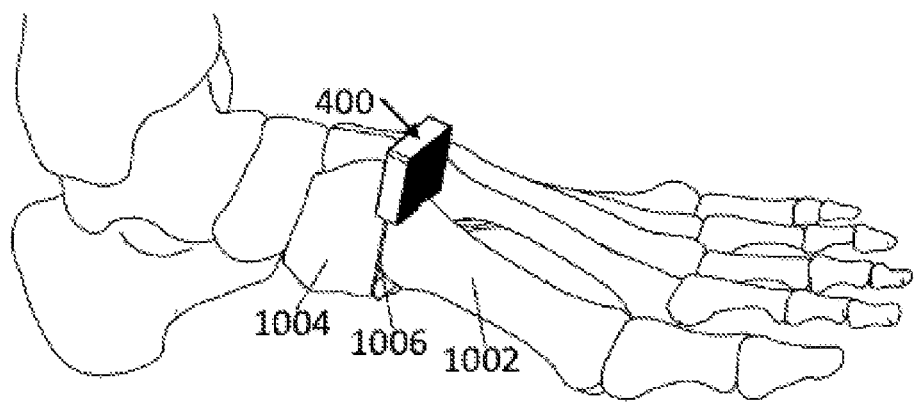
FIGS. 10A through 10G are schematic diagrams illustrating various embodiments of the surgical system.
Figure 10B:
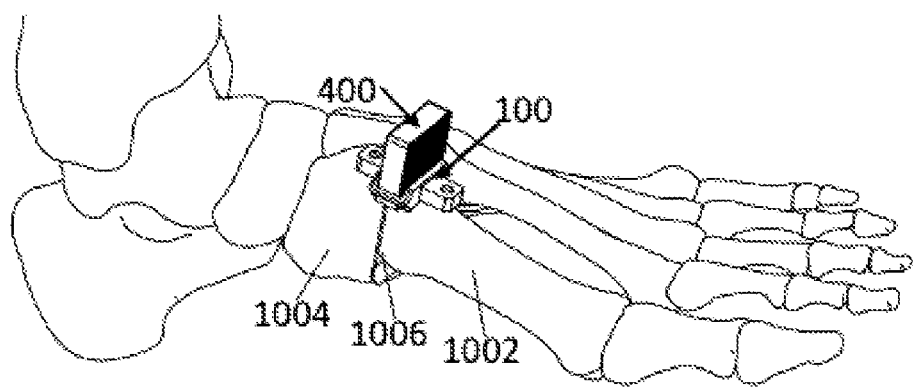
Figure 10C:
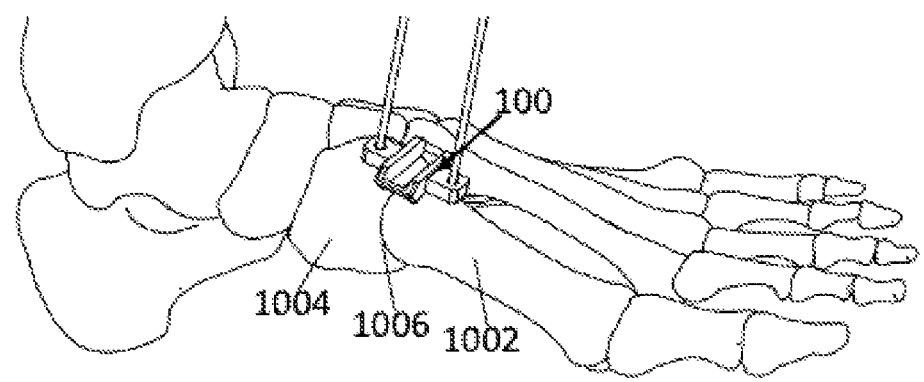
Figure 10D:
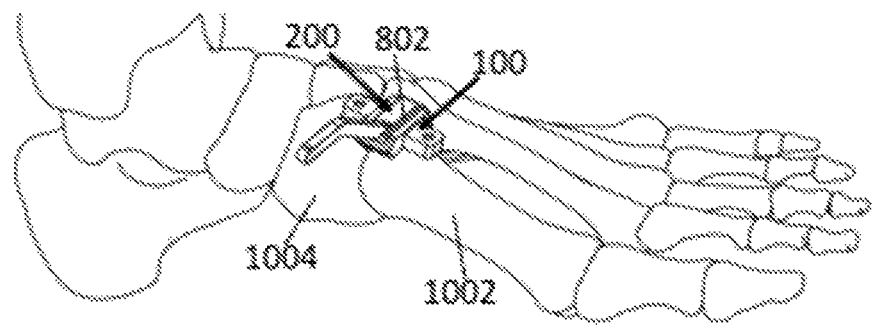
Figure 10E:
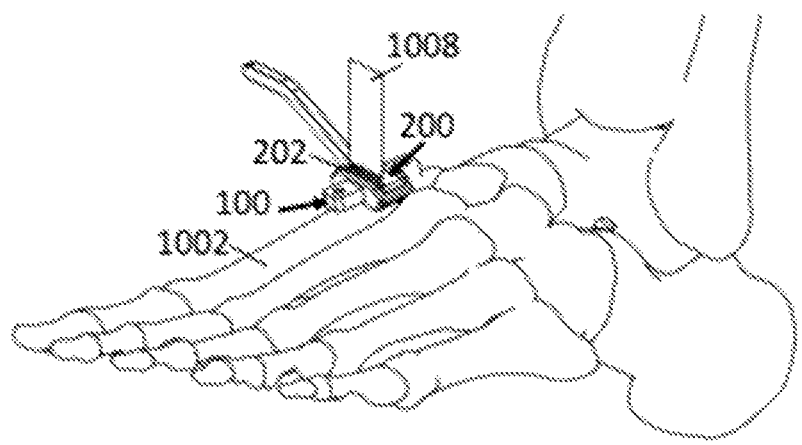
Figure 11B:
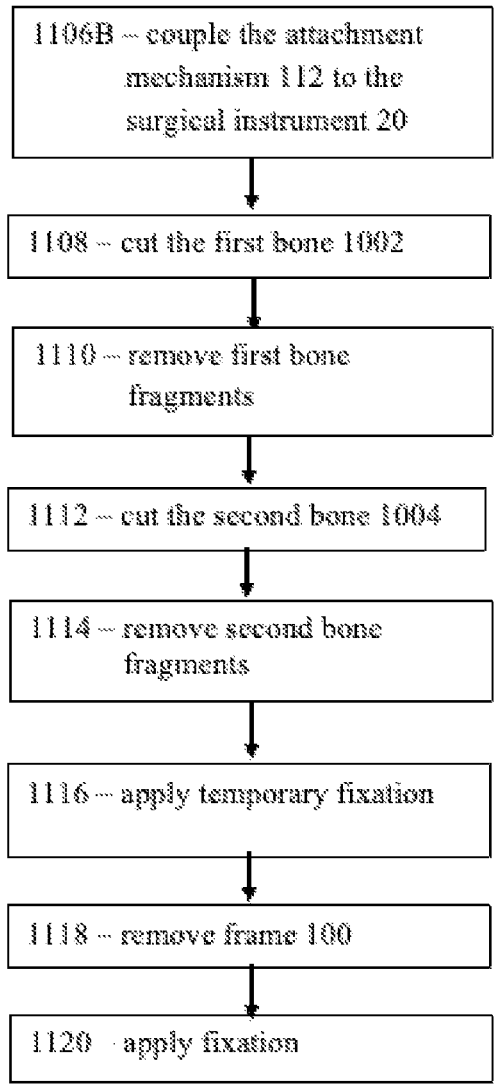

The first bone 1002 can be cut (step 1310) with the cutting instrument 1008 (e.g., see FIG. 10E). The cutting instrument 1008 can be held against the cut guide first side 202 to assist in keeping it straight and avoid the cutting instrument 1008 jumping or skiving and damaging bone and/or tissue near the osteotomy site.

If desired, bone fragments from the first bone 1002 can be removed from the osteotomy site. The bone fragments can be removed in any suitable manner, such as through the window 110.

Figure 10F:
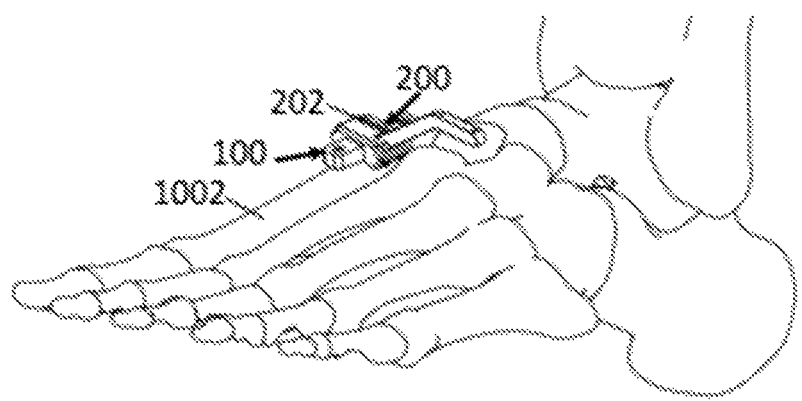

The cut guide 200 can be removed, reversed, and replaced in the window 110, orienting the cut guide first side 202 over the second bone 1004 (step 1308B) (e.g., see FIG. 10F). This can be done without removing the frame 100 which is advantageous because it minimizes time spent on the osteotomy and reduces the risk of misalignment. Additionally, the cut guide 200 can be reversed and replaced in the window 110, or another cut guide 200 can be selected from the kit of cut guides 200.

The second bone 1004 can be cut with the cutting instrument 1008 (step 1312). The cutting instrument 1008 can be held against the cut guide first side 202 to assist in keeping the cutting instrument 1008 straight and to keep the cutting instrument 1008 from jumping or skiving and damaging bone and/or tissue near the osteotomy site.

The cut guide 200 can be removed from the frame 100 (step 1314). If desired, bone fragments from the second bone 1004 can be removed by any suitable means, such as, through the window 110.

(Step 1316) The first bone 1002 and the second bone 1004 can be compressed together and temporary fixation applied. Temporary fixation can be any means that will keep the bones in place while their position is checked. Temporary fixation can be the placement of K-wires and/or olive pins, locking of the surgical instrument 20, among other means possible and contemplated herein.

Bone positions can be checked. Checking the bone positions can include checking the position of the first bone 1002 relative to surrounding bones and/or tissues, checking the position of the second bone 1004 relative to surrounding bones and/or tissues, and checking the position of the first bone 1002 and the second bone 104 relative to each other. Bone positions can be checked using fluoroscopy, physical examination, visual examination, among other techniques that are possible and contemplated herein.

The frame 100 can be removed (step 1318). When using fluoroscopy, if the frame 100 is comprised of radio-opaque materials it may be removed after checking bone positions; if the frame 100 is not comprised of radio-opaque materials it may be removed before checking bone positions.

Figure 10G:
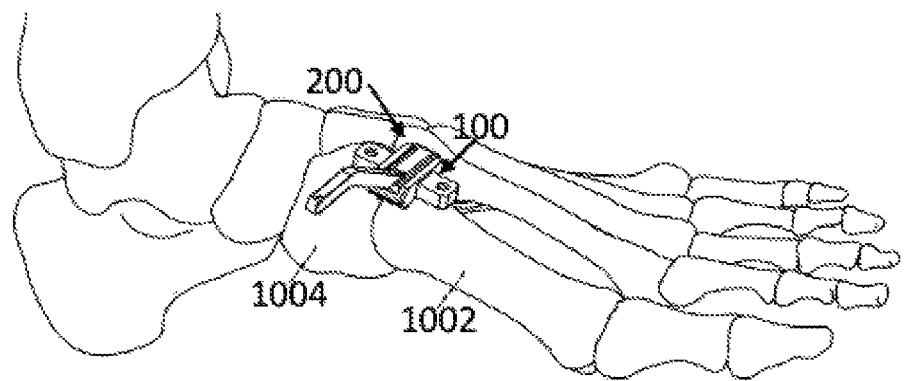
Figure 10H:
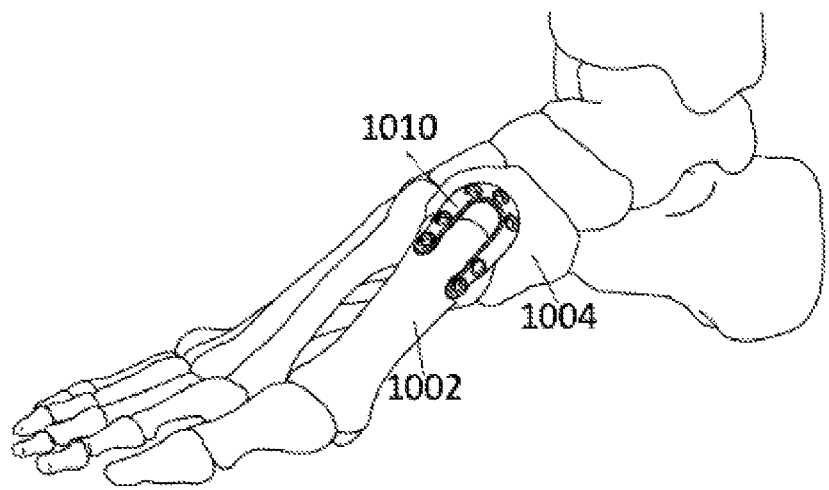
FIG. 10H is a schematic diagram of a fixation device on the foot.

The first bone 1002 and the second bone 1004 can be fixed by applying the fixation device 1010 to the first bone 1002 and to the second bone 1004 (e.g., see FIG. 10H).

Figure 13B:
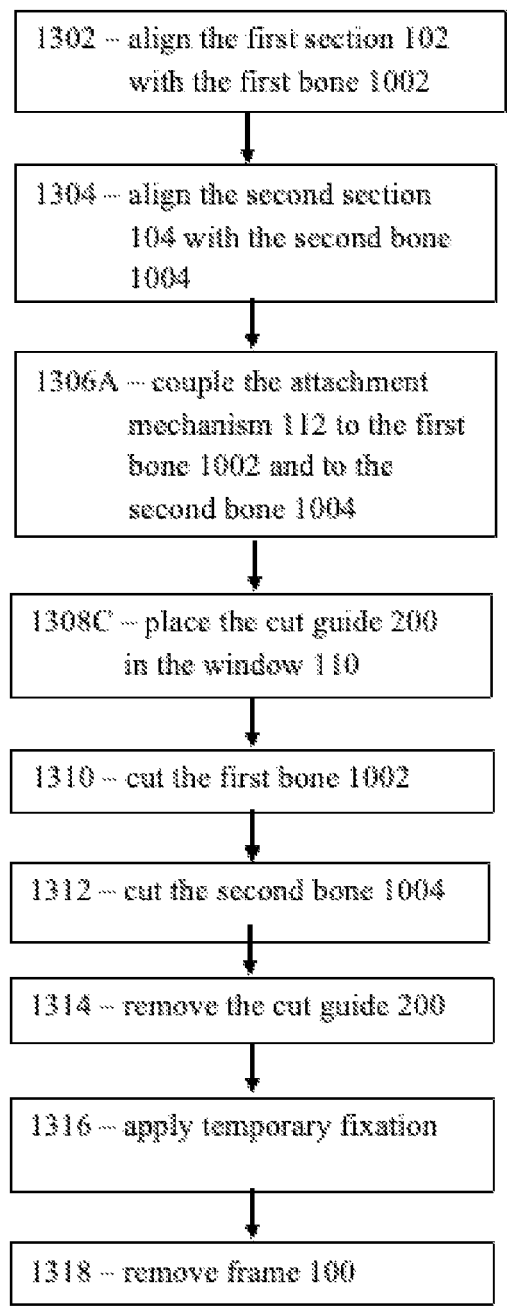

In additional or alternative embodiments, the method of performing an osteotomy (FIG. 13B) can include aligning the first section 102 of the frame 100 over a first bone 1002 (step 1302). The second bone 1004 can be aligned with the second section 104 of the frame 100 (step 1304).

The frame 100 can be coupled to the first bone 1002 by coupling the attachment mechanism 112 to the first bone 1002. The frame 100 can be coupled to the second bone 1004 by coupling the attachment mechanism 112 to the second bone 1004. (Step 1306A) (e.g. see FIG. 10C).

The cut guide 200 can be placed in the window 110 (step 1308C) orienting the cut guide first side 202 over the first bone 1002 and the cut guide second side 204 over the second bone 1004 (e.g., see Figure G). In some embodiments the cut guide 200 can be selected from a kit of cut guides 200.

The first bone 1002 can be cut (step 1310) with the cutting instrument 1008. The cutting instrument 1008 can be held against the cut guide first side 202 to assist in keeping cutting instrument 1008 straight and keep the cutting instrument 1008 from jumping or skiving and damaging bone and/or tissue near the osteotomy site.

If desired, bone fragments from the first bone 1002 can be removed from the osteotomy site. The bone fragments can be removed in any suitable manner, such as through the window 110.

The second bone 1004 can be cut (step 1312). The second bone 1004 can be cut with the cutting instrument 1008. The cutting instrument 1008 can be held against the cut guide second side 204 to assist in keeping the cutting instrument 1008 straight and to keep the cutting instrument 1008 from jumping or skiving and damaging bone and/or tissue near the osteotomy site.

The cut guide 200 can be removed from the frame 100 (step 1314).

If desired, bone fragments from the second bone 1004 can be removed by any suitable means, such as, through the window 110.

(Step 1316). The first bone 1002 and the second bone 1004 can be compressed together and temporary fixation applied. Temporary fixation can be any means that will keep the bones in place while their position is checked. Temporary fixation can be the placement of K-wires and/or olive pins, locking of the surgical instrument 20, among other means possible and contemplated herein.

Bone positions can be checked. Checking the bone positions can include checking the position of the first bone 1002 relative to surrounding bones and/or tissues, checking the position of the second bone 1004 relative to surrounding bones and/or tissues, and checking the position of the first bone 1002 and the second bone 104 relative to each other. Bone positions can be checked using fluoroscopy, physical examination, visual examination, among other techniques that are possible and contemplated herein.

The frame 100 can be removed (step 1318). When using fluoroscopy, if the frame 100 is comprised of radio-opaque materials it may be removed after checking bone positions; if the frame 100 is not comprised of radio-opaque materials it may be removed before checking bone positions.

The first bone 1002 and the second bone 1004 can be fixed by applying the fixation device 1010 to the first bone 1002 and the second bone 1004 (e.g., see FIG. 10H).

Figure 13C:
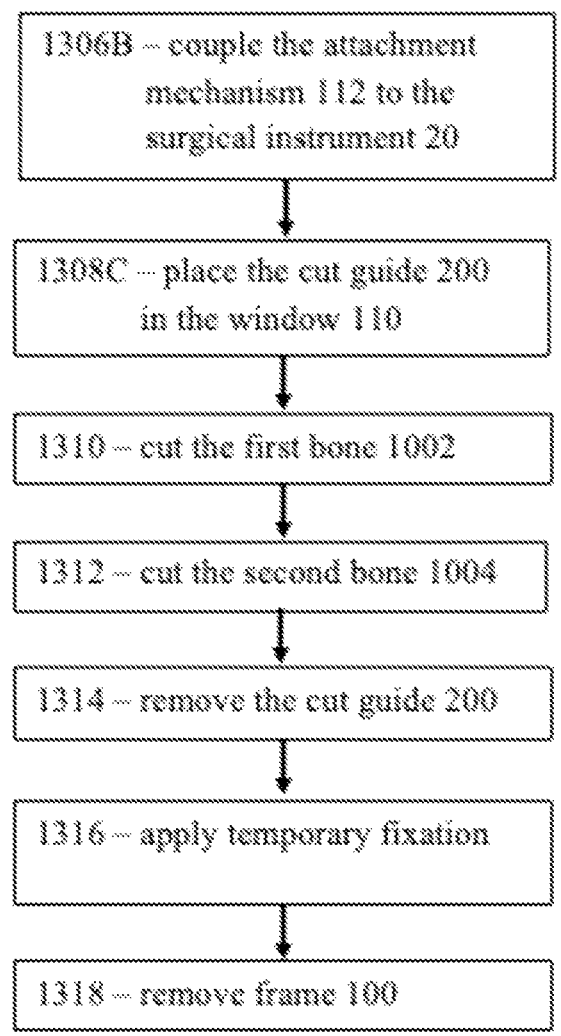

In additional or alternative embodiments, the method of performing an osteotomy (FIG. 13C) can include coupling the attachment mechanism 112 to the surgical instrument 20 (e.g., see FIG. 1F) which places the first section 102 over the first bone 1002 and the second section 104 over the second bone 1004 (step 1306B). The second bone 1004 can be aligned with the second section 104 of the frame 100 (step 1304). The cut guide 200 can be placed in the window 110 (step 1308C), orienting the cut guide first side 202 over the first bone 1002 and the cut guide second side 204 over the second bone 2004 (e.g., see FIG. 10G). In some embodiments the cut guide 200 can be selected from a kit of cut guides 200.

The first bone 1002 can be cut (step 1310) with the cutting instrument 1008. The cutting instrument 1008 can be held against the cut guide first side 202 to assist in keeping the cutting instrument 1008 straight and keep cutting instrument 1008 from jumping or skiving and damaging bone and/or tissue near the osteotomy site.

If desired, the bone fragments from the first bone 1002 can be removed from the osteotomy site. The bone fragments can be removed in any suitable manner, such as through the window 110 by removing and replacing the cut guide 200.

The second bone 1004 can be cut by any cutting means (step 1312). The second bone 1004 can be cut with the cutting instrument 1008. The cutting instrument 1008 can be held against the cut guide second side 204 to assist in keeping the cutting instrument 1008 straight and to keep the cutting instrument 1008 from jumping or skiving and damaging bone and/or tissue near the osteotomy site.

The cut guide 200 can be removed from the frame 100 (step 1314). If desired, bone fragments from the second bone 1004 can be removed by any suitable means, such as, through the window 110.

(step 1316) The first bone 1002 and the second bone 1004 can be compressed together and temporary fixation applied. Temporary fixation can be any means that will keep the bones in place while their position is checked. Temporary fixation can be the placement of K-wires and/or olive pins, locking of the surgical instrument 20, among other means possible and contemplated herein.

Bone positions can be checked. Checking the bone positions can include checking the position of the first bone 1002 relative to surrounding bones and/or tissues, checking the position of the second bone 1004 relative to surrounding bones and/or tissues, and checking the position of the first bone 1002 and the second bone 104 relative to each other. Bone positions can be checked using fluoroscopy, physical examination, visual examination, among other techniques that are possible and contemplated herein.

The frame 100 can be removed (step 1318). When using fluoroscopy, if the frame 100 is comprised of radio-opaque materials it may be removed after checking bone positions; if the frame 100 is not comprised of radio-opaque materials it may be removed before checking bone positions.

The bones 1002 and 1004 can be fixed by applying at least one fixation device 1010. The at least one fixation device 1010 can be applied to the first bone 1002 and applied to the second bone 1004 (e.g., see FIG. 10H).

In additional or alternative embodiments, the method of performing an osteotomy (FIG. 14A) can include placing the aligner 400 in a target joint 1006 (step 1402) (e.g., see FIG. 10A). The target joint 1006 can be the space between the first bone 1002 and the second bone 1004. When the first bone 1002 and the second bone 1004 are different bones, the target joint 1006 is the joint between them. When the first bone 1002 and the second bone 1004 are different bone portions, then the target joint 1006 is the space where the two bone portions meet, for example, the space can be a fracture site or osteotomy site. The aligner 400 can be placed in the target joint 1006 by placing the shim 402 in the target joint 1006.

The frame 100 can be positioned over the target joint 1006 by placing it over the aligner 400 (step 1404) (e.g., see FIG. 10B), positioning the first section 102 over the first bone 1002 and the second section 104 over the second bone 1004.

The frame 100 can be coupled to the first bone 1002 by coupling the attachment mechanism 112 to the first bone 1002. The frame 100 can be coupled to the second bone 1004 by coupling the attachment mechanism 112 to the second bone 1004. (Step 1406A) (e.g. see FIG. 10C).

(Step 1408) The aligner can be removed by any suitable means, including pulling it up through the window 110.

(Step 1410) The first bone 1002 can be cut by any cutting means. The first bone 1002 can be cut with the cutting instrument 1008. The cutting instrument 1008 can be held against the frame first side 802 to assist in keeping the cutting instrument 1008 straight and avoid the cutting instrument 1008 jumping or skiving and damaging the tissue surround the osteotomy site.

If desired, the bone fragments from the first bone 1002 can be removed from the osteotomy site. The bone fragments can be removed in any suitable manner. In some embodiments the bone fragments can be removed through the window 110.

(Step 1412) The second bone 1004 can be cut by any cutting means. The second bone 1004 can be cut with the cutting instrument 1008. The cutting instrument 1008 can be held against the frame second side 804 to assist in keeping the cutting instrument 1008 straight and avoid the cutting instrument 1008 jumping or skiving and damaging the tissue surround the osteotomy site.

If desired, the bone fragments from the second bone 1004 can be removed. The bone fragments can be removed in any suitable manner. In some embodiments the bone fragments can be removed through the window 110.

(Step 1416) The first bone 1002 and the second bone 1004 can be compressed together and temporary fixation applied. Temporary fixation can be any means that will keep the bones in place while their position is checked. Temporary fixation can be the placement of K-wires and/or olive pins, locking of the surgical instrument 20, among other means possible and contemplated herein.

Bone positions can be checked. Checking the bone positions can include checking the position of the first bone 1002 relative to surrounding bones and/or tissues, checking the position of the second bone 1004 relative to surrounding bones and/or tissues, and checking the position of the first bone 1002 and the second bone 104 relative to each other. Bone positions can be checked using fluoroscopy, physical examination, visual examination, among other techniques that are possible and contemplated herein.

The frame 100 can be removed (step 1418). When using fluoroscopy, if the frame 100 is comprised of radio-opaque materials it may be removed after checking bone positions; if the frame 100 is not comprised of radio-opaque materials it may be removed before checking bone positions.

The bones 1002 and 1004 can be fixed by applying at least one fixation device 1010 (step 1214). The at least one fixation device 1010 can be applied to the first bone 1002 and applied to the second bone 1004 (e.g., see FIG. 10H).

In additional or alternative embodiments, the method of performing an osteotomy (FIG. 14B) can include placing the aligner 400 in a target joint 1006 (step 1402) (e.g., see FIG. 10A). The aligner 400 can be placed in the target joint 1006 by placing the shim 402 in the target joint 1006.

The frame 100 can be positioned over the target joint 1006 by placing it over the aligner 400 (step 1404) (e.g., see FIG. 10B), positioning the first section 102 over the first bone 1002 and the second section 104 over the second bone 1004.

(Step 1406B) The frame 100 can be coupled to the surgical instrument 20 by coupling the attachment mechanism 112 to the surgical instrument 20. (e.g. see FIG. 10C).

(Step 1408) The aligner can be removed by any suitable means, including pulling it up through the window 110.

(Step 1410) The first bone 1002 can be cut by any cutting means. The first bone 1002 can be cut with the cutting instrument 1008. The cutting instrument 1008 can be held against the frame first side 802 to assist in keeping the cutting instrument 1008 straight and avoid the cutting instrument 1008 jumping or skiving and damaging the tissue surround the osteotomy site.

If desired, the bone fragments from the first bone 1002 can be removed from the osteotomy site. The bone fragments can be removed in any suitable manner. In some embodiments the bone fragments can be removed through the window 110.

(Step 1412) The second bone 1004 can be cut by any cutting means. The second bone 1004 can be cut with the cutting instrument 1008. The cutting instrument 1008 can be held against the frame second side 804 to assist in keeping the cutting instrument 1008 straight and avoid the cutting instrument 1008 jumping or skiving and damaging the tissue surround the osteotomy site.

If desired, the bone fragments from the second bone 1004 can be removed. The bone fragments can be removed in any suitable manner. In some embodiments the bone fragments can be removed through the window 110.

(Step 1416) The first bone 1002 and the second bone 1004 can be compressed together and temporary fixation applied. Temporary fixation can be any means that will keep the bones in place while their position is checked. Temporary fixation can be the placement of K-wires and/or olive pins, locking of the surgical instrument 20, among other means possible and contemplated herein.

Bone positions can be checked. Checking the bone positions can include checking the position of the first bone 1002 relative to surrounding bones and/or tissues, checking the position of the second bone 1004 relative to surrounding bones and/or tissues, and checking the position of the first bone 1002 and the second bone 104 relative to each other. Bone positions can be checked using fluoroscopy, physical examination, visual examination, among other techniques that are possible and contemplated herein.

(Step 1418) The bones 1002 and 1004 can be fixed by applying at least one fixation device 1010 (step 1214). The at least one fixation device 1010 can be applied to the first bone 1002 and applied to the second bone 1004 (e.g., see FIG. 10H).

Figure 15A:
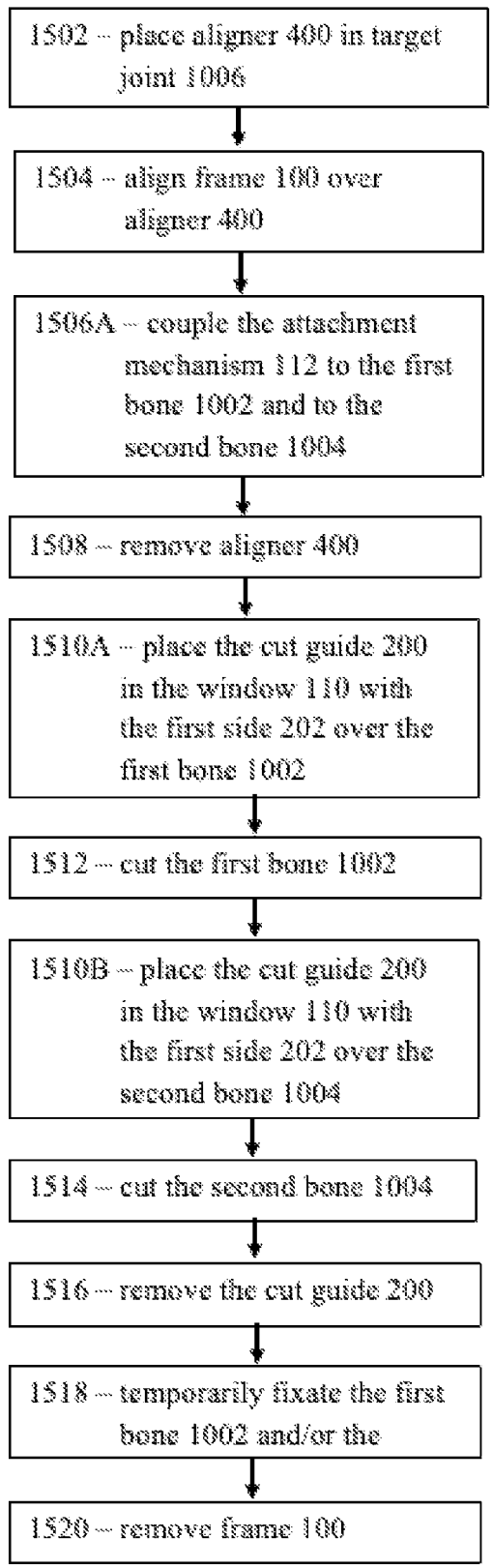
FIGS. 15A through 15B are flow charts illustrating embodiments of performing an osteotomy with the frame, the cut guide, and the aligner.

In additional or alternative embodiments, the method of performing an osteotomy (FIG. 15A) can include placing the aligner 400 in a target joint 1006 (step 1502) (e.g., see FIG. 10A). The aligner 400 can be placed in the target joint 1006 by placing the shim 402 in the target joint 1006. The frame 100 can then be positioned over the target joint 1006 by placing it over the aligner 400 (step 1504) (e.g., see FIG. 10B), positioning the first section 102 over the first bone 1002 and the second section 104 over the second bone 1004.

The frame 100 can be coupled to the first bone 1002 by coupling the attachment mechanism 112 to the first bone 1002. The frame 100 can be coupled to the second bone 1004 by coupling the attachment mechanism 112 to the second bone 1004. (Step 1506A) (e.g. see FIG. 10C).

(Step 1508) The aligner can be removed by any suitable means, including pulling it up through the window 110.

(Step 1510A) The cut guide 200 can be placed in the window 110 orienting the cut guide first side 202 over the first bone 1002 (e.g., see FIGS. 10D and 10E). In some embodiments the cut guide 200 can be selected from a kit of cut guides 200.

The first bone 1002 can be cut (step 1512) with the cutting instrument 1008. The cutting instrument 1008 can be held against the cut guide first side 202 to assist in keeping it straight and avoid the cutting instrument 1008 jumping or skiving and damaging bone and/or tissue near the osteotomy site.

If desired, the bone fragments from the first bone 1002 can be removed from the osteotomy site. The bone fragments can be removed in any suitable manner, such as through the window 110.

(Step 1510B) The cut guide 200 can be removed, reversed, and replaced orienting the cut guide first side 202 over the second bone 1004 (step 1510B) (e.g., see FIG. 10DF). In some embodiments the cut guide 200 can be replaced with a different cut guide 200 selected from a kit of cut guides 200.

(Step 1514) The second bone 1004 can be cut by any cutting means. The second bone 1004 can be cut with the cutting instrument 1008. The cutting instrument 1008 can be held against the cut guide first side 202 to assist in keeping the cutting instrument 1008 straight and to keep the cutting instrument 1008 from jumping or skiving and damaging bone and/or tissue near the osteotomy site.

The cut guide 200 can be removed from the frame 100 (step 1516). If desired, the bone fragments from the second bone 1004 can be removed by any suitable means, such as, through the window 110.

The first bone 1002 and the second bone 1004 can be compressed together and temporary fixation applied (step 1518). Temporary fixation can be any means that will keep the bones in place while their position is checked. Temporary fixation can be the placement of K-wires and/or olive pins, locking of the surgical instrument 20, among other means possible and contemplated herein.

Bone positions can be checked. Checking the bone positions can include checking the position of the first bone 1002 relative to surrounding bones and/or tissues, checking the position of the second bone 1004 relative to surrounding bones and/or tissues, and checking the position of the first bone 1002 and the second bone 104 relative to each other. Bone positions can be checked using fluoroscopy, physical examination, visual examination, among other techniques that are possible and contemplated herein.

The frame 100 can be removed (step 1520). When using fluoroscopy, if the frame 100 is comprised of radio-opaque materials it may be removed after checking bone positions; if the frame 100 is not comprised of radio-opaque materials it may be removed before checking bone positions.

The first bone 1002 and the second bone 1004 can be fixed by applying the fixation device 1010 to the first bone 1002 and the second bone 1004 (e.g., see FIG. 10H).

Figure 15B:
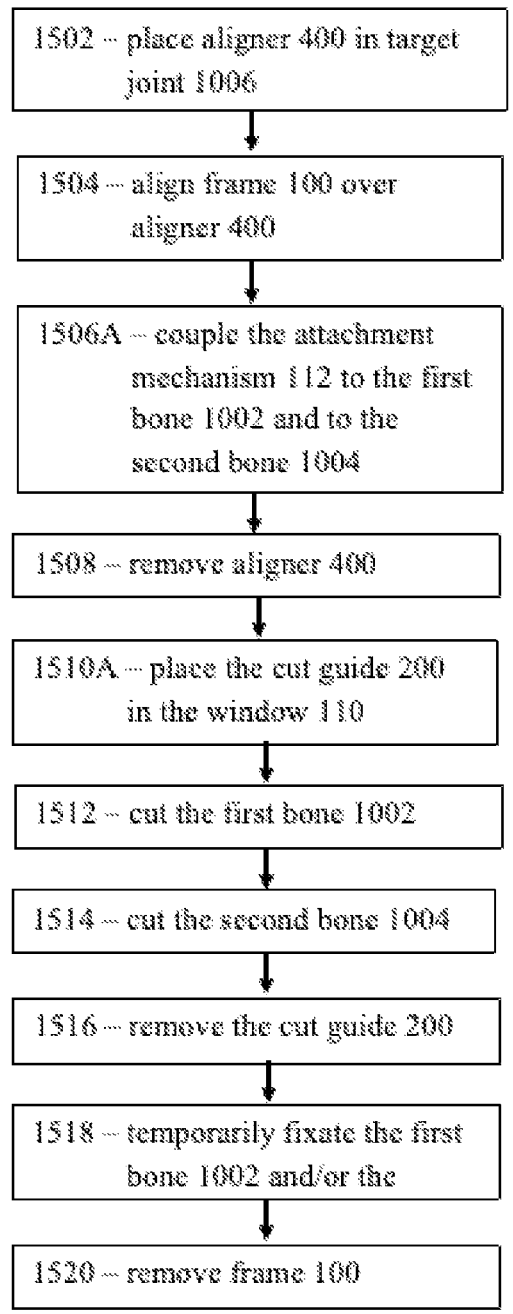

In additional or alternative embodiments, the method of performing an osteotomy (FIG. 15B) can include placing the aligner 400 in a target joint 1006 (step 1502) (e.g., see FIG. 10A). The aligner 400 can be placed in the target joint 1006 by placing the shim 402 in the target joint 1006.

The frame 100 can be positioned over the target joint 1006 by placing it over the aligner 400 (step 1504) (e.g., see FIG. 10B), positioning the first section 102 over the first bone 1002 and the second section 104 over the second bone 1004.

The frame 100 can be coupled to the first bone 1002 by coupling the attachment mechanism 112 to the first bone 1002. The frame 100 can be coupled to the second bone 1004 by coupling the attachment mechanism 112 to the second bone 1004 (step 1506A).

(Step 1508) The aligner can be removed by any suitable means, including pulling it up through the window 110.

(Step 1510A) The cut guide 200 can be placed in the window 110, orienting the cut guide first side 202 over the first bone 1002 and the cut guide second side 204 over the second bone 1004 (e.g., see FIG. 10G). In some embodiments the cut guide 200 can be selected from a kit of cut guides 200.

The first bone 1002 can be cut (step 1512) by any cutting means. The first bone 1002 can be cut with the cutting instrument 1008. The cutting instrument 1008 can be held against the cut guide first side 202 to assist in keeping it straight and avoid the cutting instrument 1008 jumping or skiving and damaging bone and/or tissue near the osteotomy site.

If desired, the cut guide 200 can be removed from the frame 100 and bone fragments from the first bone 1002 can be removed from the osteotomy site. The bone fragments can be removed in any suitable manner, such as through the window 110.

(Step 1514) The second bone 1004 can be cut by any cutting means. The second bone 1004 can be cut with the cutting instrument 1008. The cutting instrument 1008 can be held against the cut guide second side 204 to assist in keeping the cutting instrument 1008 straight and to keep the cutting instrument 1008 from jumping or skiving and damaging bone and/or tissue near the osteotomy site.

The cut guide 200 can be removed from the frame 100 (step 1516). If desired, the bone fragments from the second bone 1004 can be removed by any suitable means, such as, through the window 110.

The first bone 1002 and the second bone 1004 can be compressed together and temporary fixation applied (step 1518). Temporary fixation can be any means that will keep the bones in place while their position is checked. Temporary fixation can be the placement of K-wires and/or olive pins, locking of the surgical instrument 20, among other means possible and contemplated herein.

Bone positions can be checked. Checking the bone positions can include checking the position of the first bone 1002 relative to surrounding bones and/or tissues, checking the position of the second bone 1004 relative to surrounding bones and/or tissues, and checking the position of the first bone 1002 and the second bone 104 relative to each other. Bone positions can be checked using fluoroscopy, physical examination, visual examination, among other techniques that are possible and contemplated herein.

The frame 100 can be removed (step 1520). When using fluoroscopy, if the frame 100 is comprised of radio-opaque materials it may be removed after checking bone positions; if the frame 100 is not comprised of radio-opaque materials it may be removed before checking bone positions.

The first bone 1002 and the second bone 1004 can be fixed by applying the fixation device 1010 to the first bone 1002 and the second bone 1004 (e.g., see FIG. 10H).

In additional or alternative embodiments, the method of performing an osteotomy (FIG. 16A) can include placing the aligner 400 (coupled to, or integral with, the frame 100) in the target joint 1006 (step 1602) against a cut end of the first bone 1002.

(Step 1604A) The frame 100 can be coupled to the first bone 1002 by coupling the attachment mechanism 112 to the first bone 1002. The frame 100 can be coupled to the second bone 1004 by coupling the attachment mechanism 112 to the second bone 1004.

(Step 1610) The second bone 1004 can be cut by any cutting means. The second bone 1004 can be cut with the cutting instrument 1008. The cutting instrument 1008 can be held against the cut guide second side 204 to assist in keeping the cutting instrument 1008 straight and to keep the cutting instrument 1008 from jumping or skiving and damaging bone and/or tissue near the osteotomy site.

The first bone 1002 and the second bone 1004 can be compressed together and temporary fixation applied (step 1614). Temporary fixation can be any means that will keep the bones in place while their position is checked. Temporary fixation can be the placement of K-wires and/or olive pins, locking of the surgical instrument 20, among other means possible and contemplated herein.

Bone positions can be checked. Checking the bone positions can include checking the position of the first bone 1002 relative to surrounding bones and/or tissues, checking the position of the second bone 1004 relative to surrounding bones and/or tissues, and checking the position of the first bone 1002 and the second bone 104 relative to each other. Bone positions can be checked using fluoroscopy, physical examination, visual examination, among other techniques that are possible and contemplated herein.

The frame 100 can be removed (step 1616). When using fluoroscopy, if the frame 100 is comprised of radio-opaque materials it may be removed after checking bone positions; if the frame 100 is not comprised of radio-opaque materials it may be removed before checking bone positions.

The first bone 1002 and the second bone 1004 can be fixed by applying the fixation device 1010 to the first bone 1002 and the second bone 1004 (e.g., see FIG. 10H).

In additional or alternative embodiments, the method of performing an osteotomy (FIG. 16B) can include placing the aligner 400 (coupled to, or integral with, the frame 100) in the target joint 1006 (step 1602) against the cut end of the first bone 1002.

The frame 100 can be coupled to the surgical instrument 20 by coupling the attachment mechanism 112 to the surgical instrument 20 (step 1604B).

(Step 1606A) The cut guide 200 can be placed in the window 110, orienting the cut guide first side 202 over the first bone 1002 and the cut guide second side 204 over the second bone 1004 (e.g., see FIG. 10G). In some embodiments the cut guide 200 can be selected from a kit of cut guides 200.

The first bone 1002 can be cut (step 1608) by any cutting means. The first bone 1002 can be cut with the cutting instrument 1008. The cutting instrument 1008 can be held against the cut guide first side 202 to assist in keeping it straight and avoid the cutting instrument 1008 jumping or skiving and damaging bone and/or tissue near the osteotomy site.

If desired, the cut guide 200 can be removed from the frame 100 and bone fragments from the first bone 1002 can be removed from the osteotomy site. The bone fragments can be removed in any suitable manner, such as through the window 110.

(Step 1610) The second bone 1004 can be cut by any cutting means. The second bone 1004 can be cut with the cutting instrument 1008. The cutting instrument 1008 can be held against the cut guide second side 204 to assist in keeping the cutting instrument 1008 straight and to keep the cutting instrument 1008 from jumping or skiving and damaging bone and/or tissue near the osteotomy site.

The cut guide 200 can be removed from the frame 100 (step 1516). If desired, the bone fragments from the second bone 1004 can be removed by any suitable means, such as, through the window 110.

The first bone 1002 and the second bone 1004 can be compressed together and temporary fixation applied (step 1614). Temporary fixation can be any means that will keep the bones in place while their position is checked. Temporary fixation can be the placement of K-wires and/or olive pins, locking of the surgical instrument 20, among other means possible and contemplated herein.

Bone positions can be checked. Checking the bone positions can include checking the position of the first bone 1002 relative to surrounding bones and/or tissues, checking the position of the second bone 1004 relative to surrounding bones and/or tissues, and checking the position of the first bone 1002 and the second bone 104 relative to each other. Bone positions can be checked using fluoroscopy, physical examination, visual examination, among other techniques that are possible and contemplated herein.

The frame 100 can be removed (step 1616). When using fluoroscopy, if the frame 100 is comprised of radio-opaque materials it may be removed after checking bone positions; if the frame 100 is not comprised of radio-opaque materials it may be removed before checking bone positions.

The first bone 1002 and the second bone 1004 can be fixed by applying the fixation device 1010 to the first bone 1002 and the second bone 1004 (e.g., see FIG. 10H).

In additional or alternative embodiments, the method of performing an osteotomy (FIG. 16C) can include placing the aligner 400 (coupled to, or integral with, the frame 100) in a target joint 1006 (step 1602) against the cut end of the first bone 1002.

The frame 100 can be coupled to the first bone 1002 by coupling the attachment mechanism 112 to the first bone 1002. The frame 100 can be coupled to the second bone 1004 by coupling the attachment mechanism 112 to the second bone 1004. (Step 1604A).

(Step 1606A) The cut guide 200 can be placed in the window 110 orienting the cut guide first side 202 over the second bone 1004. In some embodiments the cut guide 200 can be selected from a kit of cut guides 200.

(Step 1610) The second bone 1004 can be cut by any cutting means. The second bone 1004 can be cut with the cutting instrument 1008. The cutting instrument 1008 can be held against the cut guide first side 202 to assist in keeping the cutting instrument 1008 straight and to keep the cutting instrument 1008 from jumping or skiving and damaging bone and/or tissue near the osteotomy site.

The cut guide 200 can be removed from the frame 100 (step 1612). If desired, the bone fragments from the second bone 1004 can be removed by any suitable means, such as, through the window 110.

The first bone 1002 and the second bone 1004 can be compressed together and temporary fixation applied (step 1614). Temporary fixation can be any means that will keep the bones in place while their position is checked. Temporary fixation can be the placement of K-wires and/or olive pins, locking of the surgical instrument 20, among other means possible and contemplated herein.

Bone positions can be checked. Checking the bone positions can include checking the position of the first bone 1002 relative to surrounding bones and/or tissues, checking the position of the second bone 1004 relative to surrounding bones and/or tissues, and checking the position of the first bone 1002 and the second bone 104 relative to each other. Bone positions can be checked using fluoroscopy, physical examination, visual examination, among other techniques that are possible and contemplated herein.

The frame 100 can be removed (step 1616). When using fluoroscopy, if the frame 100 is comprised of radio-opaque materials it may be removed after checking bone positions; if the frame 100 is not comprised of radio-opaque materials it may be removed before checking bone positions.

The first bone 1002 and the second bone 1004 can be fixed by applying the fixation device 1010 to the first bone 1002 and the second bone 1004 (e.g., see FIG. 10H).

One advantage of the frame 100 spanning the joint is that it allows for good visibility of the joint without removing the frame 100. It also allows for the removal of bone fragments without removing the frame 100. It also allows a surgeon to cut the ideal amount of bone based on patient anatomy because the bones are visible while the cut is being made.

The various embodiments discussed herein may be practiced in other specific forms and the described embodiments are to be considered in all respects only as illustrative, and not restrictive. The scope of the technology is, therefore, indicated by the appended claims rather than by the foregoing description. All changes that come within the meaning and range of equivalency of the claims are to be embraced within their scope. That is, one of ordinary skill in the art will appreciate that modifications and/or adaptations to the various aspects may be made without departing from the scope of the present technology, as set forth in the following claims.

What is claimed is:

1. A surgical apparatus comprising:
    a first section, a second section, a third section, and a fourth section defining a single quadrilateral window therebetween, wherein:
        the first section is configured to align with a first bone, wherein the first bone is a metatarsal;
        the second section is configured to align with a second bone, wherein the second bone is a cuneiform, and
        the window includes a size configured to span a target joint between the first bone and the second bone when the first section is aligned with the first bone and the second section is aligned with the second bone to provide surgical access to the target joint;
        the single quadrilateral window comprises at least one attachment mechanism coupled to the first section, and at least one attachment mechanism coupled to the second section; and
    a frame bottom configured to conform to the shape of at least one bone.

2. The surgical apparatus of claim 1, wherein the attachment mechanism is configured to couple at least one of the first section, and the second section, the third section, and the fourth section to at least one of a surgical jig, the first bone, and the second bone.

3. The surgical apparatus of claim 1, further comprising at least one radiograph positioning tool.

4. The surgical apparatus of claim 1, further comprising a cut guide, wherein the cut guide comprises a head, wherein the head is comprised of a first member and a second member.

5. The surgical apparatus of claim 4, wherein the first member is coupled to and perpendicular to the second member.

6. The surgical apparatus of claim 5, wherein the head further comprises a third member parallel to the first member, perpendicular to the second member, and coupled to the second member.

7. The surgical apparatus of claim 4, wherein:
    the first section and the second section are separated by a first width,
    the first member comprises a second width, wherein
        the second width is less than the first width such that the head fits within the window and contacts at least a portion of the first section, the second section, the third section, and the fourth section.

8. The surgical apparatus of claim 7, wherein the head further comprises a third member, wherein the third member comprises a third width and the third width is less than the first width such that the head fits within the window and contacts at least a portion of the first section, the second section, the third section, and the fourth section.

9. The surgical apparatus of claim 7, wherein the second member comprises a fourth width that is less than the second width and the second member is centered within the second width.

10. The surgical apparatus of claim 4, wherein the cut guide further comprises a placement device.

11. The surgical apparatus of claim 10, wherein the placement device comprises at least one of a handle, a handlebar, a magnet, a bar, a knob, a hold, a grip, a shaft, and a tab.

12. The surgical apparatus of claim 1, further comprising a detachable aligner, wherein the detachable aligner comprises a grip.

13. The surgical apparatus of claim 12, wherein
    the first section and the second section are separated by a first width;
    the grip comprises a grip depth that is less than the first width such that the grip fits within the window and contacts at least a portion of the first section, the second section, the third section, and the fourth section.

14. The surgical apparatus of claim 12, wherein the grip at least partially comprises a high friction surface.

15. The surgical apparatus of claim 12, further comprising a shim.

16. The surgical apparatus of claim 15, wherein the shim comprises a shim depth that is less than or equal to the grip depth.

17. The surgical apparatus of claim 16, wherein the shim depth is uniform.

18. The surgical apparatus of claim 16, wherein the shim depth is at least partially tapered.

19. The surgical apparatus of claim 16, wherein the shim is centered on the grip.

20. A surgical apparatus comprising:
    a frame comprising:
        a first section, a second section separated by a first width from the first section, a third section, and a fourth section defining a single quadrilateral window therebetween, wherein:
            the first section is configured to align with a first bone, wherein the first bone is a metatarsal;
            the second section is configured to align with a second bone, wherein the second bone is a cuneiform; and
            the window includes a size configured to span a target joint between the first bone and the second bone when the first section is aligned with the first bone and the second section is aligned with the second bone to provide surgical access to the target joint;
            the single quadrilateral window comprises at least one attachment mechanism coupled to the first section, and at least one attachment mechanism coupled to the second section;
            wherein the at least one attachment mechanism is configured to couple the frame to at least one of a surgical jig, the first bone, and the second bone;
    a frame bottom configured to conform to the shape of at least one bone;
    at least one circular aperture radiograph positioning tool;
    a cut guide comprising a placement device, and a head comprising a second width, wherein the second width is less than the first width such that the head fits within the window; and
    a detachable aligner comprising a grip and a shim.

* * * * *